Figure 1:
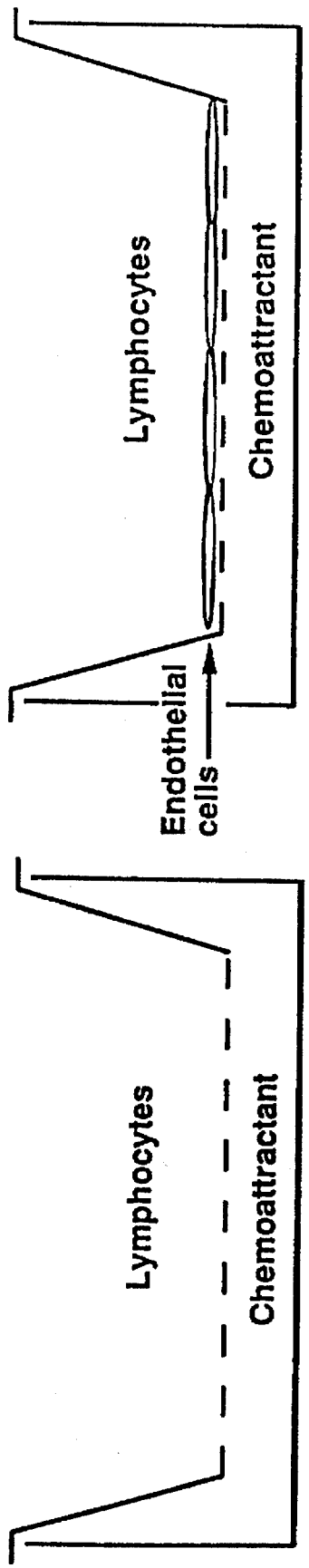

United States Patent [19]

Springer et al.

[11] Patent Number: 5,514,555
[45] Date of Patent: May 7, 1996

[54] ASSAYS AND THERAPEUTIC METHODS BASED ON LYMPHOCYTE CHEMOATTRACTANTS

[75] Inventors: Timothy A. Springer, Chestnut Hill; Stephen J. Roth, Brookline; Michelle W. Carr, Boston, all of Mass.

[73] Assignee: Center for Blood Research, Inc., Boston, Mass.

[21] Appl. No.: 30,764

[22] Filed: Mar. 12, 1993

[51] Int. Cl.[6] ........................... C12Q 1/02; G01N 33/567
[52] U.S. Cl. .................. 435/7.24; 435/29; 435/240.241; 436/63; 436/503
[58] Field of Search ..................... 435/7.24, 29, 240.241, 435/240.242, 284, 285; 436/63, 503

[56] References Cited

U.S. PATENT DOCUMENTS

| | | | |
|---|---|---|---|
| 4,912,057 | 3/1990 | Guirguis et al. | 435/285 |
| 5,026,649 | 6/1991 | Lyman et al. | 435/284 |
| 5,122,470 | 6/1992 | Banes | 435/240.241 |
| 5,175,092 | 12/1992 | Gabriels, Jr. et al. | 435/29 |
| 5,190,878 | 3/1993 | Wilhelm | 435/285 |
| 5,210,021 | 5/1993 | Goodwin, Jr. | 435/29 |
| 5,260,210 | 11/1993 | Rubin et al. | 435/240.241 |
| 5,302,515 | 4/1994 | Goodwin, Jr. | 435/29 |

FOREIGN PATENT DOCUMENTS

| | | |
|---|---|---|
| WO90/08777 | 8/1990 | WIPO. |
| WO91/08231 | 6/1991 | WIPO. |

OTHER PUBLICATIONS

Colotta et al., 1992, "Expression of a monocyte chemotactic cytokine by human mononuclear phagocytes," J. Immunol. 148:760–765.
Decock et al., 1990, "Identification of the monocyte chemotactic protein from human osteosarcoma cells and monocytes: detection of a novel n-terminally processed form," Biochem. and Biophys. Res. Comm. 167:904–909.
Graves et al., 1989, "Identification of monocyte chemotactic activity produced by malignant cells," Science 245:1490–1493.
Graves and Valente, 1991, "Monocyte chemotactic proteins from human tumor cells," Biochem. Pharmacol. 41:333–337.
Jiang et al., 1990, "Post-translational modified of a monocyte-specific chemoattractant synthesized by glioma, osteosarcoma, and vascular smooth muscle cells," J. Biol. Chem. 265:18318–18321.
Jiang et al., 1992, "Monocyte chemoattractant protein–1 regulates adhesion molecule expression and cytokine production in human monocytes," J. Immunol. 148:2423–2428.
Jones and Warren, 1992, "Monocyte chemoattractant protein 1 in a rat model of pulmonary granulomatosis," Lab. Invest. 66:498–503.

(List continued on next page.)

*Primary Examiner*—David Saunders
*Attorney, Agent, or Firm*—Pennie & Edmonds

[57] ABSTRACT

The present invention relates to a novel assay for lymphocyte chemotaxis. The assay is transendothelial assay using endothelial cells cultured on microporous filters. Lymphocyte transmigration through the filter toward a suspected chemoattractant is measured. Apparatuses for carrying out the assay are also provided. The apparatuses and methods of the present invention can be used for the identification of inhibitors (e.g., antagonists) or promoters (chemoattractants) of the adhesion receptor-mediated migration of leukocytes through the endothelium (extravasation). Such inhibitors and promoters respectively inhibit and promote the inflammatory response, and thus have therapeutic utilities. The inhibitors and promoters are identified by detecting their abilities to respectively inhibit or promote the chemotaxis of lymphocytes in the assay of the invention. The assay of the invention also has diagnostic utilities for detecting a disease or disorder involving a defect in lymphocyte chemotaxis. In a specific embodiment, the invention provides a novel lymphocyte chemoattractant, termed LCA, of molecular weight of about 14,500±3,000 daltons. Derivatives and analogs of LCA, and antibodies and antibody fragments thereto are also provided. The invention also relates to therapeutic uses and compositions related to the foregoing.

23 Claims, 12 Drawing Sheets

OTHER PUBLICATIONS

Jones et al., 1992, "Potential role of monocyte chemoattractant protein 1/JE in monocyte/macrophage–dependent IgA immune complex alveolitis in the rat," J. Immunol. 149:2147–2154.

Koch et al., 1992, "Enhanced production of monocyte chemoattractant protein–1 in rheumatoid arthritis," J. Clin. Invest. 90:772–779.

Kunkel et al., 1991, "Stimuls specific induction of monocyte chemotactic protein–1 (MCP–1) gene expression," in *Chemotactic Cytokines*, Westwick et al. (eds.), Plenum Press, New York, pp. 65–71.

Leonard and Yoshimura, 1990, "Human monocyte chemoattractant protein–1 (MCP–1)," Immunol. Today 11:97–101.

Leonard et al., 1991, "Biological aspects of monocyte chemoattractant protein–1 (MCP–1)," in *Chemotactic Cytokines*, Westwick et al. (eds.), Plenum Press, New York, pp. 57–64.

Nelken et al., 1991, "Monocyte chemoattractant protein–1 in human atheromatous plaques," J. Clin. Invest. 88:1121–1127.

Oppenheimer–Marks et al., 1990, "Human T lymphocyte adhesion to endothelial cells and transendothelial migration," J. Immunol. 145:140–148.

Oppenheimer–Marks and Ziff, 1988, "Migration of lymphocytes through endothelial cell monolayers: augmentation by interferon-y," Cell. Immunol. 114:307–323.

Paine et al., 1993, "MCP–1 expression by rat type II alveolar epithelial cells in primary culture," J. Immunol. 150:4561–4570.

Robinson et al., 1989, "Complete amino acid sequence of a human monocyte chemoattractant,a putative mediator of cellular immune reactions," Proc. Natl. Acad. Sci. USA 86:1850–1854.

Rovin et al., 1992, "Cytokine–induced production of monocyte chemoattractant protein–1 by cultured human mesangial cells," J. Immunol. 148:2148–2153.

Schall, 1991, "Biology of the Rantes/SIS cytokine family," Cytokine 3:165–183.

Sica et al., 1990, "Monocyte chemotactic and activating factor gene expression induced in endothelial cells by IL–1 and tumor necrosis factor," J. Immunol. 144:3034–3038.

Standiford et al., 1991, "Alveolar macrophage–derived cytokines induce monocyte chemoattractant protein–1 expression from human pulmonary type II–like epithelial cells," J. Biol. Chem. 266:9912–9918.

Valente et al., 1991, "Characterization of monocyte chemotactic protein–1 binding to human monocytes," Biochem. and Biophys. Res. Comm. 176:309–314.

Villiger et al., 1992, "Production of monocyte chemoattractant protein–1 by inflamed synovial tissue and cultured synoviocytes," J. Immunol. 149:722–727.

Ylä–Herttuala et al., 1991, "Expression of monocyte chemoattracant protein 1 in macrophage–rich areas of human and rabbit atherosclerotic lesions," Proc. Natl. Acad. Sci. USA 88:5252–5256.

Yoshimura and Leonard, 1990, "Identification of high affinity receptors for human monocyte chemoattractant protein–1 on human monocytes," J. Immunol. 145:292–297.

Yoshimura and Leonard, 1991, "Human monocyte chemoattractant protein–1 (MCP–1)," in *Chemotactic Cytokines*, Westwick et al. (eds.), Plenum Press, New York, pp.47–56.

Yoshimura and Leonard, 1992, "Human Monocyte chemoattractant protein–1: structure and function," in *Interleukin 8 (NAP–1) and Related Chemotactic Cytokines*, Baggiolini and Sorg, (eds.), Basel, Karger, pp. 131–152.

Yoshimura et al., 1989, "Purification and amino acid analysis of two human monocyte chemoattractants produced by phytohemagglutinin–stimulated human blood mononuclear leukocytes," J. Immunol. 142:1956–1962.

Anderson and Springer, 1987, Leukocyte adhesion deficiency: an inherited defect in the Mac–1, LFA–1, and p. 150,95 glycoproteins, Ann. Rev. Med. 38:175–194.

Bach and Voynow, 1966, One–way stimulation in mixed leukocyte cultures, Science 153:545–547.

Bacon et al., 1990, Stimulation of lymphocyte migration by a novel low–molecular weight compound in normal human skin and plasma, Eur. J. Immunol. 20:565–571.

Bacon and Camp, 1990, Lipid lymphocyte chemoattractants in psoriasis, Prostaglandins, 40:603–614.

Baggiolini et al., 1989, Neutrophil–activating peptide–1/interleukin 8, a novel cytokine that activates neutrophils, J. Clin. Invest. 84:104514 1049.

Barker et al., 1991, Modulation of keratinocyte–derived interleukin–8 which is chemotactic for neutrophils and T lymphocytes, Amer. J. of Path. 139:869–876.

Berman et al., 1984, Functional characteristics of histamine receptor–bearing mononuclear cells. Identification and characterization of two histamine–induced human lymphokines that inhibit lymphocyte migration, J. Immunol. 133:1495–1504.

Berman et al., 1988, Lymphocyte motility and lymphocyte chemoattractant factors, Immunol. Invest. 17:625–677.

Berman et al., 1990, Lymphocyte recruitment to the the lung, Am. Rev. Respir, Dis. 142:238–257.

Boulay et al., 1990, Synthesis and use of a novel N–formyl peptide derivative to isolate a human N–formyl peptide receptor cDNA, Biochem. Biophys. Res. Commun. 168:1103–1109.

Braun and Unanue, 1983, Surface immunoglobulin and the lymphocyte cytoskelton, Fed. Proc. 42:2446–2451.

Braun and Unanue, 1983, The lymphocyte cytoskeleton and its control of surface receptor functions, Sem. in Hemat. 20:322–333.

Bretscher, 1984,Endocytosis: relation to capping and cell locomotion, Science 224:681–686.

Brown and Gallin, 1988, Chemotactic disorders, Hematology/Oncology Clinics of N. Amer. 2:61–79.

Butcher, 1991, Leukocyte–endothelial cell recognition: Three (or more) steps to specificity and diversity, Cell 67:1033–1036.

Capsoni et al., 1989, A new simplified single–filter assay for 'in vitro' evaluation of chemotaxis of $^{51}$Cr–labeled polymorphonuclear leukocytes, J. Immunol. Methods 120:125–131.

Casale and Abbas, 1990, Comparison of leukotriene $B_4$–induced neutrophil migration through different cellular barriers, Am. J. Physiol. 258:C639–C647.

Center and Cruikshank, 1982, Modulation of lymphocyte migration by human lymphokines. I. Identification and characterization of chemoattractant activity for lymphocytes from mitogen–stimulated mononuclear cells, J. Immunol. 128:2563–2568.

Center et al., 1983, Functional characteristics of histamine receptor–bearing mononuclear cells. Selective production of lymphocyte chemoattractant lymphokines with histamine used as a ligand, J. Immunol. 131:1854–1859.

Champion et al., 1986, The embryonic thymus produces chemotactic peptides involved in the homing of hemopoietic precursors, Cell 44:781–790.

Clinchy et al., 1991, T and B cell collaboration: induction of motilty in small, resting B cells by interleukin 4, Eur. J. Immunol. 21:1445–1451.

Cruikshank and Center, 1982, Modulation of lymphocyte migration by human lymphokines, J. Immunol. 128:2569–2574.

Cruikshank et al., 1987, Lymphokine activation of T4$^+$ T lymphocytes and monocytes, J. Immunol. 138:3817–3823.

Cruikshank et al., 1991, Lymphocyte chemoattractant factor induces CD4–dependent intracytoplasmic signaling in lymphocytes. J. Immunol. 146:2928–2934.

Dahlgren et al., 1987, Chemotactic factor binding and functional capacity: a comparison between human granulocytes and differentiated HL–60 cells, J. Leukocyte Biol. 42:245–252.

DeBono, 1976, Endothelial–lymphocyte interactions in vitro. Adherence of nonallergised lymphocytes, Cell. Immunol. 26:78–88.

de Fougerolles et al., 1991, Characterization of ICAM–2 and evidence for a third counter–receptor for LFA–1, J. Exp. Med. 174:253–267.

Detmers et al., 1990, Neutrophil–activating protein 1/interleukin 8 stimulates the binding activity of the leukocyte adhesion receptor CD11b/CD18 on human neutrophils, J. Exp. Med. 171:1155–1162.

Devreotes and Zigmond, 1988, Chemotaxis in eukaryotic cells: A focus on leukocytes and dictyostelium, Ann. Rev. Cell Biol. 4:649–686.

Dohlman et al., 1991, Model systems for the study of seven–transmembrane–segment receptors, Ann. Rev. Biochem. 60:653–688.

Dustin and Springer, 1988, Lymphocyte function associated antigen–1 (LFA–1) interaction with intercellular adhesion molecule–1 (ICAM–1) is one of at least three mechanisms for lymphocyte adhesion to cultured endothelial cells, J. Cell Biol. 107:321–331.

Foegh, 1989, Eicosanoids and platelet–activating factor, in Xenograft 25, Mark A. Hardy (eds), Elsevier Science Publishers, pp. 171–179.

Gallin et al., 1980, Disorders of phagocyte chemotaxis, Ann. Int. Med.92:520–538. Gerard and Gerard, 1991, The chemotactic receptor for human C5a anaphylatoxin, Nature 349:614–617.

Gilman, 1987, G proteins: Transducers of receptor–generated signals, Ann. Rev. Biochem. 56:615–649.

Gronenborn and Clore, 1991, Modeling the three–dimensional structure of the monocyte chemoattractant and activating protein MCAF/MCP–1 on the basis of the solution structure of interleukin–8, Protein Eng. 4:263–269.

Gupta et al., 1979, Subpopulations of human T lymphocytes. T cells with receptors for IgM or IgG and Locomotion of T and non–T cells in peripheral blood from patients with chronic mucocutaneous candidiasis, Clin. Immunol. and Immunopath. 14:86–95.

Harlan et al., 1991, In vivo models of leukocyte adherence to endothelium. In Adhesion: Its Role in Inflammatory Disease, J. R. Harlan and D. Liu, eds. (W. H. Freeman & Co.), pp. 117–150.

Huber et al., 1991, Regulation of transendothelial neutrophil migration by endogenous interleukin–8, Science 254:99–102.

Huber and Weiss, 1989, Disruption of the subendothelial basement membrane during neutrophil diapedesis in an in vitro construct of a blood vessel wall, J. Clin. Invest.83:1122–1136.

Jalkanen et al., 1987, Human lymphocyte and lymphoma homing receptors, Ann. Rev. Med. 38:467–476.

Kameyoshi et al., 1992, Cytokine RANTES released by thrombin–stimulated platelets is a potent attractant for human eosinophils, J. Exp. Med. 176:587–592.

Kaplan and Silverberg, 1988, Mediators of inflammation: an overview, Meth. Enzymol. 163:3–23.

Katz et al., 1991, Serotonin induction of a novel T–cell activating factor from human aortic endothelial cells, Amer. Rev. of Resp. Dis. 143:A238.

Kavanaugh et al., 1991, Role of CD11/CD18 in adhesion and transendothelial migration of T cells: Analysis utilizing CD18–deficient T cell clones, J. Immunol. 146:4149–4156.

Kendall, 1991, Functional anatomy of the thymic microenvironment, J. Anat. 177:1–29.

Kudo et al., 1991, Inhibition of IL–8–induced W3/25$^+$ (CD4$^+$) T lymphocyte recruitment into subcutaneous tissues of rats by selective depletion of in vivo neutrophils with a monoclonal antibody, J. Immunol. 147:2196–2201.

Kuijpers et al., 1992, Neutrophil migration across monolayers of cytokine–prestimulated endothelial cells: a role for platelet-activating factor and IL–8, J. Cell Biol. 117:565–572.

Larsen et al., 1989, The neutrophil–activating protein (NAP–1) is also chemotactic for T lymphocytes, Science 243:1464–1466.

Lawrence and Springer, 1991, Leukocytes roll on a selectin at physiologic flow rates: distinction from and prerequisite for adhesion through integrins, Cell 65:859–873.

Leonard et al., 1990, Leukocyte specificity and binding of human neutrophil attractant/activation protein–1, J. Immunol. 144:1323–1330.

Leonard et al., 1990, Human monocyte chemoattractant protein–1 (MCP–1). Immunol. Today 11:97–101.

Leonard et al., 1991, Neutrophil recruitment by intradermally injected neutrophil attractant/activation protein–1. J. Invest. Dermatol. 96:690–694.

Loor, 1980, Plasma membrane and cell cortex interactions in lymphocyte functions, Adv. Immunol. 30:1–120.

Masuyama et al., 1992, Evidence for recent as well as long term activation of T cells migrating through endothelial cell monolayers in vitro, J. Immunol. 148:1367–1374.

Matsushima et al., 1988, Molecular cloning of a human monocyte–derived neutrophil chemotactic factor (MDNCF) and the induction of MDNCF mRNA by interleukin 1 and tumor necrosis factor, J. Exp. Med. 167:1883–1893.

McFadden and Fraher, 1990, Inhibitors of membrane transmethylation reactions prevent the lymphocyte chemokinetic response, Immunol. Lett. 26:211–216.

McFadden et al., 1991, Lymphocyte chemokinetic factors derived from human tonsils: modulation by 1,25–dihyroxyvitamin $D_3$ (calcitriol), Am. J. Respir. Cell Mol. Biol. 4:42–49.

Naccache, 1987, Cell movement, excitability, and contractility, Int. Rev. Cytol. Supp. 17:457–492.

Odlander et al., 1989, Formation and effects of leukotriene $B_4$ in human lymphocytes, Int. J. Tiss. Reac. XI(6):277–289.

Oppenheim et al., 1991, Properties of the novel proinflammatory supergene "intercrine" cytokine family, Annu. Rev. Immunol. 9:617–648.

Parrott and Wilkinson, 1981, Lymphocyte locomotion and migration, Prog. Allergy 28:193–284.

Partsch et al., 1989, Modulation of the migration and chemotaxis of PMN cells by hyaluronic acid, Z. Rheumatol.

48:123–128.

Pereira et al., 1990, CAP37, a human neutrophil–derived chemotactic factor with monocyte specific activity, J. Clin. Invest. 85:1468–1476.

Pober and Cotran, 1990, The role of endothelial cells in inflammation, Transplantation 50:537–544.

Pohajdak et al., 1986, Chemotaxis of large granular lymphocytes, J. Immunol. 136:278–284.

Potter and Van Epps, 1987, Separation and purification of lymphocyte chemotactic factor (LCF) and interleukin 2 produced by human peripheral blood mononuclear cells, Cell. Immunol. 105:9–22.

Rand et al., 1991, CD4–mediated stimulation of human eosinophils: lymphoyte chemoattractant factor and other CD4–binding ligands elicit eosinophil migration, J. Exp. Med. 173:1521–1528.

Russell et al., 1975, Chemotaxis of lymphoblasts, Nature 256:646–648.

Sandborg and Smolen, 1988, Early biochemical events in leukocyte activation, Lab. Invest. 59:300–320.

Savagner et al., 1988, Aspects of haemopoietic cell dynamics: ontogeny and targeted migration, Ann. Inst. Pasteur/Immunol. 139:409–431.

Schall et al., 1990, Selective attraction of monocytes and T lymphocytes of the memory phenotype by ctyokine RANTES, Nature 347:669–671.

Schleimer and Rutledge, 1986, Cultured human vascular endothelial cells acquire adhesiveness for neutrophils after stimulation with interleukin 1, endotoxin, and tumor–promoting phorbol diesters. J. Immunol. 136:649–654.

Shijubo et al., 1988, Two distinct mechanisms involved in the infiltration of lymphocytes into tumors, Jpn. J. Cancer Res. 79:1111–1118.

Shuster et al., 1992, Identification and prevalance of a genetic defect that causes leukocyte adhesion deficiency in Holstein cattle, Proc. Natl. Acad. Sci. USA 89:9225–9229.

Snyderman and Pike, 1984, Chemoattractant receptors on phagocytic cells, Ann. Rev. Immunol. 2:257–281.

Springer, 1990, Adhesion receptors of the immune system, Nature 346:425–434.

Transwell Application and Selection Guide, Costar Corporation, Nucleopore®.

Van Epps, 1982, Mediators and modulators of human lymphocyte chemotaxis, Agents Actions 12(Suppl.):217–233.

Van Epps et al., 1983, Migration of human helper/inducer T cells in response to supernatants from con A–stimulated suppressor/cytotoxic T cells, J. Immunol. 131:697–700.

Van Epps et al., 1983, Production of a human T lymphocyte chemotactic factor by T cell subpopulations, J. Immunol. 130:2727–2731.

Wilkinson et al., 1976, Chemotaxis of mitogen–activated human lymphocytes and the effects of membrane–active enzymes, Clin. Exp. Immunol. 25:280–287.

Wilkinson et al., 1977, Antigen–induced locomotor responses in lymphocytes, J. Exp. Med. 145:1158–1168.

Wright, et al., 1988, Leukocyte chemoattraction by 1,2–diacylglycerol, Proc. Natl. Acad. Sci. USA, 85:1869–1873.

Yoshimura et al., 1987, Purification of a human monocyte–derived neutrophil chemotactic factor that has peptide sequence similarity to other host defense cytokines, Proc. Natl. Acad. Sci. USA 84:9233–9237.

Zigmond and Hirsch, 1973, Leukocyte locomotion and chemotaxis. New methods for evaluation, and demonstration of a cell–derived chemotactic factor, J. Exp. Med. 137:387–410.

Degranges et al., 1992, "Extracellular matrix covered biomaterials for human endothelial cell growth," Int. J. Artif. Organs 15(12):722–726.

Engelmann and Friedl, 1989, "Optimization of culture conditions for human corneal endothelial cells," In Vitro Cell. & Dev. Biol. 25(11):1065–1072.

Solomon, 1992, "The seeding of human aortic endothelial cells on the extra–cellular matrix of human umbilical vein endothelial cells," Int. J. Exp. Path. 73:491–501.

Stedman's Medical Dictionary, 1990, 25th Ed., Williams & Wilkins, p. 1624.

ASSAYS AND THERAPEUTIC METHODS BASED ON LYMPHOCYTE CHEMOATTRACTANTS

This invention was made with government support under grant number CA 31798 awarded by the National Institutes of Health. The Government has certain rights in the invention.

TABLE OF CONTENTS

1. INTRODUCTION
2. BACKGROUND OF THE INVENTION
3. SUMMARY OF THE INVENTION
   3.1. DEFINITIONS
4. DESCRIPTION OF THE FIGURES
5. DETAILED DESCRIPTION OF THE INVENTION
   5.1. A TRANSENDOTHELIAL LYMPHOCYTE CHEMOTAXIS ASSAY
   5.2. IDENTIFICATION OF PROMOTERS OF LYMPHOCYTE CHEMOTAXIS
      5.2.1. LCA, A NOVEL LYMPHOCYTE CHEMOATTRACTANT
      5.2.2. DERIVATIVES AND ANALOGS OF LCA
      5.2.3. ASSAYS OF LCA AND ITS DERIVATIVES AND ANALOGS
   5.3. IDENTIFICATION OF INHIBITORS OF LYMPHOCYTE CHEMOTAXIS
   5.4. GENERATION AND USE OF ANTIBODIES TO LYMPHOCYTE CHEMOATTRACTANTS AND CHEMOTAXIS INHIBITORS
   5.5. THERAPEUTIC USES OF LYMPHOCYTE CHEMOATTRACTANTS, CHEMOTAXIS INHIBITORS, AND ANTIBODIES TO THE FOREGOING
      5.5.1. DEMONSTRATION OF THERAPEUTIC UTILITY
      5.5.2. THERAPEUTIC ADMINISTRATION AND COMPOSITIONS
   5.6. DIAGNOSTIC UTILITIES
6. A TRANSENDOTHELIAL LYMPHOCYTE CHEMOTAXIS ASSAY
7. CHARACTERIZATION OF A NOVEL LYMPHOCYTE CHEMOATTRACTANT

1. INTRODUCTION

The present invention relates to a novel assay for lymphocyte chemotaxis. The assay of the invention provides methods for screening for promoters (e.g., chemoattractants) and inhibitors (e.g., antagonists of chemoattractants) of lymphocyte chemotaxis. A novel lymphocyte chemoattractant, antibodies thereto, and therapeutic methods and compositions are also provided.

2. BACKGROUND OF THE INVENTION

Migration of leukocytes from blood vessels into diseased tissues is crucial to the initiation of normal disease-fighting inflammatory responses. But this process, known as leukocyte recruitment, is also involved in the onset and progression of debilitating and life-threatening inflammatory and autoimmune diseases. The pathology of these diseases results from the attack of the body's immune system defenses on normal tissues. Thus, blocking leukocyte recruitment to target tissues in inflammatory and autoimmune disease would be a highly effective therapeutic intervention. The leukocyte cell classes that participate in cellular immune responses include lymphocytes, monocytes, neutrophils, eosinophils and mast cells. Lymphocytes are "master cells" that control the activity of most of these other cell types, particularly the monocytes. Lymphocytes are the leukocyte class that initiate, coordinate, and maintain the inflammatory response, and thus are the most important cells to block from entering inflammatory sites. Lymphocytes attract monocytes to the site, which are responsible for much of the actual tissue damage that occurs in inflammatory disease. Infiltration of these cells is responsible for a wide range of chronic, autoimmune diseases, and also organ transplant rejection. These diseases include rheumatoid arthritis, psoriasis, contact dermatitis, inflammatory bowel disease, multiple sclerosis, atherosclerosis, sarcoidosis, idiopathic pulmonary fibrosis, dermatomyositis, hepatitis, diabetes, allograft rejection, and graft-versus-host disease.

This process by which leukocytes leave the bloodstream and accumulate at inflammatory sites, and initiate disease, is best understood for neutrophils and monocytes, but is likely to be similar in broad outline for lymphocytes. This process takes place in at least three distinct steps (Springer, T. A., 1990, Nature 346:425–33; Lawrence and Springer, 1991, Cell 65:859–73; Butcher, E. C., 1991, Cell 67:1033–36). It is mediated at a molecular level by chemoattractant receptors, by cell-surface proteins called adhesion molecules, and by the ligands that bind to these two classes of cell-surface receptor. The major types of adhesion molecules are known as "selectins", "integrins" and "immunoglobulin (Ig) family" receptors.

Each of the three steps is essential for the emigration of the leukocytes to target tissues. Blocking the steps has been shown to prevent a normal inflammatory response, and impedes abnormal responses of inflammatory and autoimmune diseases (Harlan et al., 1992, In vivo models of leukocyte adherence to endothelium. In Adhesion: Its Role in Inflammatory Disease., J. M. Harlan and D. Y. Liu, (eds.), W. H. Freeman & Co., pp. 117–150). The steps of leukocyte adhesion and transendothelial migration can be summarized as follows:

Step 1. Primary adhesion. Leukocytes attach loosely to the blood vessel endothelium and "roll" slowly along the blood vessel wall, pushed by the flow of blood. Leukocyte-endothelium attachment is mediated by cell surface adhesion molecules called "selectins" which bind to carbohydrate-rich ligands ("glycoconjugates") on the leukocyte cell surface.

Step 2. Activation of leukocytes and migration to the target site. Chemoattractant receptors on the surface of the leukocytes bind chemoattractants secreted by cells at the site of damage or infection. Receptor binding activates the immune defenses of the leukocytes, and activates the adhesiveness of the adhesion molecules that mediate Step 3.

Step 3. Attachment and transendothelial migration. The leukocytes bind very tightly to the endothelial wall of the blood vessel and move to the junction between endothelial cells, where they begin to squeeze between these cells to reach the target tissue. This tighter binding is mediated by binding to adhesion receptors called "integrins" on the leukocytes to complementary receptors of the "Ig family" on the endothelium. (The Ig family molecules are named for their similarity to antibody molecules (immunoglobulins)). Chemoattractant receptors are also involved at this stage, as the leukocytes migrate up a concentration gradient of the chemoattractant secreted by cells at the target site.

These three classes of receptor-ligand interactions are all required and appear to act in a highly cooperative and coordinated manner to mediate leukocyte adherence to the microvasculature, diapedesis, and subsequent leukocyte mediated injury to tissue in inflammatory disease.

LFA-1 and Mac-1 together with p150,95 comprise the leukocyte integrins, a subfamily of integrins that share a common β subunit (CD18) and have distinct αL, αM and αX (CD11a, b and c) α subunits (reviewed in Larson and Springer, 1990, Immunol. Rev. 114:181–217; Springer, 1990, Nature 346:425–433). They are required for leukocyte emigration as demonstrated by an absence of neutrophil extravasation (1) in patients with mutations in the common β subunit (leukocyte adhesion deficiency), and (2) after treatment of healthy neutrophils with a monoclonal antibody (mAb) to the common β subunit in vivo or in vitro (reviewed in Anderson and Springer, 1987, Ann. Rev. Med. 38:175–194; Larson and Springer, 1990, Immunol. Rev. 114:181–217).

The integrins LFA (lymphocyte function-associated antigen)-1 and Mac-1 on the neutrophil bind to the Ig family member ICAM (intercellular adhesion molecule)-1 on endothelium (Smith et al., 1988, J. Clin. Invest. 82:1746–1756; Smith et al., 1989, J. Clin. Invest. 83:2008–2017; Diamond et al., 1990, J. Cell Biol. 111:3129–3139). LFA-1 and not Mac-1 binds to ICAM-2 (de Fougerolles et al., 1991, J. Exp. Med. 174:253–267; Diamond et al., 1990, J. Cell Biol. 111:3129–3139), an endothelial cell molecule that is more closely related to ICAM-1 than these molecules are to other Ig superfamily members (Staunton et al., 1989, Nature 339:61–64).

The integrin VLA-4, that contains the α4 (CD49d) subunit noncovalently associated with the β1 (CD29) subunit, is expressed by lymphocytes, monocytes, and neural crest-derived cells, and can interact with vascular cell adhesion molecule-1 (VCAM-1) (Elices et al., 1990, Cell 60:577). Like ICAM-1 and ICAM-2, VCAM-1 is a member of the Ig superfamily (Osborn et al., 1989, Cell 59:1203).

Chemoattractants are soluble mediators which activate cell adhesion and motility and direct cell migration through formation of a chemical gradient. They are produced by bacteria and numerous cell types including stimulated endothelial and stromal cells, platelets, tumor cells, cultured cell lines, and leukocytes themselves. The cells responding to chemoattractants appear to express specific receptors on their surfaces which bind the chemoattractant molecules and sense the gradient. Receptor stimulation induces cells to respond via a common signal transduction pathway which involves interaction of the chemoattractant-receptor complex with a guanine nucleotide or GTP-binding protein (G protein) (Gilman, A. G., 1987, Ann. Rev. Biochem. 56:615–49). This interaction stimulates phosphatidyl inositol hydrolysis by a phospholipase C, thus generating inositol phosphates and diacylglycerol. A transient rise in cytosolic free calcium then activates protein kinase C, and a variety of events including protein phosphorylation, membrane potential changes, and intracellular pH alterations ensue.

Several of the chemoattractants primarily affecting neutrophils were among the first chemoattractants identified. These include the complement component C5a, arachidonate derivative leukotriene $B_4$ ($LTB_4$), platelet activating factor (PAF), and formylmethionyl peptides of bacterial origin such as formyl-met-leu-phe (fMLP) (Devreotes and Zigmond, 1988, Annu. Rev. Cell Biol. 4:649–86). Although structurally dissimilar and stimulatory via separate receptors, these molecules produce a rapid and marked increase in neutrophil adhesiveness and motility leading to chemotaxis and prominent neutrophil accumulation in vivo (Pober and Cotran, 1990, Transplantation 50:537–44). The receptors for C5a and fMLP have been identified and sequenced; cDNA clones for each have also been generated (Gerard and Gerard, 1991, Nature 349:614–617; Boulay et al., 1990, Biophys. Res. Commun. 168:1103–09). These receptors share many structural features with one another and members of the "rhodopsin superfamily" of protein receptors (Dohlman et al., 1991, Ann. Rev. Biochem. 60:653–88).

More recently, a protein chemoattractant for neutrophils designated neutrophil activating protein-1 (NAP-1) or interleukin 8 (IL-8) was identified and molecularly cloned (Yoshimura et al., 1987, Proc. Natl. Acad. Sci. USA 84:9233–37; Matsushima et al., 1988, J. Exp. Med. 167:1883–93; Oppenheim et al., 1991, Annu. Rev. Immunol. 9:617–48). IL-8 was originally characterized as a 72 amino acid molecule produced by monocytes; variants of 79, 77, and 69 amino acids have subsequently been identified from additional sources including activated endothelial cells, lymphocytes, fibroblasts, and tumor lines. IL-8 has structural homology to a supergene family of novel 8–10 kDa cytokines isolated chiefly by subtractive hybridization (Oppenheim et al., 1991, Annu. Rev. Immunol. 9:617–48) and recently named the "chemokine" family. IL-8 and several other human cytokines, including platelet factor 4, basic protein, IP-10, and melanoma growth stimulating factor/GRO comprise a subfamily of chemokines located on chromosome 4. In this subfamily, the relative positions of four cysteine residues are identical, with the first two cysteine residues separated by a single amino acid (C-X-C). Disulfide bonds between these four cysteines form two loops which appear to be essential for activity. The other subfamily, which includes the monocyte chemoattractants RANTES and monocyte chemoattractant protein-1 (see below), is clustered on chromosome 17, and the first two cysteines are adjacent (C-C).

The biological profile of activity for IL-8 is similar to that for C5a, $LTB_4$, PAF, and fMLP; the respiratory burst is induced, neutrophil chemotaxis is promoted, and Mac-1 expression is increased on the surface of granulocytes (Baggiolini et al., 1989, J. Clin. Invest. 84: 1045–49; Detmers et al., 1990, J. Exp. Med. 171:1155–62). IL-8 differs from these others, however, in that it has been reported to attract approximately 10% of human peripheral blood T lymphocytes of either CD4$^+$ or CD8$^+$ subsets (Leonard et al., 1990, J. Immunol. 144:1323–30; Larsen et al., 1989, Science 241:1464–66), but does not attract monocytes. There is some controversy on whether IL-8 is a lymphocyte chemoattractant, because when injected in human skin it attracts neutrophils but not lymphocytes (Leonard et al, 1991, J. Invest. Dermatol. 96:690–94).

The chemoattractants which predominantly activate and guide monocytes include monocyte chemoattractant protein-1 (MCP-1) (Leonard and Yoshimura, 1990, Immunol. Today 11:97–101), the RANTES protein (Schall et al., 1990, Nature 347:669–71), and the neutrophil α granule protein CAP37 (Pereira et al., 1990, J. Clin. Invest. 85:1468–76), among others. As noted above, MCP-1 and RANTES are structurally homologous and belong to the subfamily of chemoattractive cytokines that are defined by a configuration of four cysteine residues in which the first two are adjacent (C-C). CAP37's structure is most homologous to proteins of the serine protease family (Peteira et al., 1990, J. Clin. Invest. 85:1468–76). The 76 amino acid MCP-1 is produced by activated endothelium, lymphocytes, macrophages, fibroblasts, smooth muscle cells, and tumor cells. It binds only to monocytes and induces approximately 30% of peripheral blood monocytes to respond in chemotaxis assays. The 68 amino acid RANTES is of special interest because it has been reported to selectively attract memory T helper cells (CD4$^+$ and UCHL1 antigen/CD45RO positive) as well as monocytes. Of the chemoattractants known to attract lymphocytes, only RANTES appears subset-selective. However, the lymphocyte chemoattractive activity of RANTES may be weaker than its activity for eosinophils (Kameyoshi et al., 1992, J. Exp. Med. 176:587–92).

Endothelial cells cultured on matrices of type I collagen have been used to study neutrophil migration toward the chemoattractant IL-8 (Huber et al., 1991, Science 254:99–102). When tested with IL-8 contained in conditioned media from stimulated endothelial cells, neutrophils migrated similarly, and there was a similar signal-to-noise ratio, on collagen matrix plus endothelium and on matrix alone. Thus, there was no indication that the assay would be improved for other cell types by adding endothelium. Indeed, the expectation would have been that neutrophils and lymphocytes would behave similarly. Lymphocyte migration across endothelium into collagen gels has previously been reported in assays of migration (Kavanaugh et al., 1991, J. Immunol. 146:4149–4156; Masuyama et al., 1992, J. Immunol. 148:1367–1374). In this system, the endothelium is cultured on a collagen gel formed on a culture dish or well for several days, then lymphocytes are added. This is an assay of migration in which there is no evidence that chemotaxis is involved; rather, it appears to assay for a migratory subset of lymphocytes. There is no teaching of a chemoauractant. Furthermore, lymphocytes migrate into collagen gels even in the absence of an endothelial cell monolayer.

Compared with neutrophil and monocyte chemoattractants, little is known about chemoattractants for lymphocytes. The best characterized lymphocyte chemoattractants are RANTES and IL-8, which primarily attract monocytes and neutrophils, as noted above. Several in vitro studies have described lymphocyte chemotactic activities in the culture supernatants of mixed lymphocyte reactions and mitogen-stimulated human peripheral blood mononuclear cells (Cruikshank and Center, 1982, J. Immunol. 128:2569; Center and Cruikshank, 1982, J. Immunol. 128:2563–68; Van Epps et al., 1983, J. Immunol. 130:2727; Van Epps et al., 1983, J. Immunol. 131:687). One of these activities was related to a protein of apparent molecular weight 14 kD named lymphocyte chemotactic factor (LCF) (Cruikshank and Center, 1982, J. Immunol. 128:2569; Center and Cruikshank, 1982, J. Immunol. 128:2563–68) that was produced by T cells (Van Epps et al., 1983, J. Immunol. 130:2727). The initial purifications of LCF possibly yielded activities contaminated by the chemotactic mediators interleukin-1 and -2 (IL-1 and IL-2), however (Cruikshank and Center, 1982, J. Immunol. 128:2569). Subsequent purifications using high performance liquid chromatography have separated IL-1 and IL-2 from a LCF 10.5 kD in size (Potter and Van Epps, 1987, Cell. Immunol. 105:9–22). This LCF attracts lymphocytes, but selective subset chemotaxis was not assessed. Further characterization of the 10.5 kD LCF, including sequence information, has not been published. Another lymphocyte chemoattractant factor has been described that is 56,000 $M_r$, binds to CD4, and is selectively chemoattractive for the CD4 subset of lymphocytes (Cruikshank et al., 1991, J. Immunol. 146:2928–34). It also is chemoattractive for monocytes (Cruikshank et al., 1991, J. Immunol. 146:2928–34) and eosinophils (Rand et al., 1991, J. Exp. Med. 173:1521–28). More recently, a less than 1 kD molecule that was extractable in lipid solvents (i.e., not a peptide) was isolated from normal human skin and named plasma-associated lymphocyte chemoattractant (Bacon et al., 1990, Eur. J. Immunol. 20:565–71). It has been suggested that this molecule is constitutively expressed in skin and accounts for surveillance lymphocyte trafficking there (Bacon et al., 1990, Eur. J. Immunol. 20:565–71). A variety of other agents or poorly characterized activities have also been reported. These include fetal calf serum, the protein casein, the mitogen phytohemagglutinin, and supernatants of stimulated peritoneal macrophages (Berman et al., 1988, Immunol. Invest. 17:625–77).

Although considerable effort has been invested on the study of lymphocyte chemoattractants, they remain poorly characterized relative to monocyte and neutrophil chemoattractants. Chemoattractants for the latter cell types, such as MCP-1 and IL-8, have been purified based on the conventional chemotaxis assay, sequenced, and cloned. However, no molecule identified primarily as a lymphocyte chemoattractive factor has been sequenced and cloned.

In large measure, the lack of rapid progress on lymphocyte chemoattractants appears due to the unreliability or lack of biological relevance of currently available lymphocyte chemotaxis assays. For example, the protein casein, fetal calf serum, the mitogen phytohemagglutinin, and the hormone insulin, have all been reported active in lymphocyte chemotaxis assays (Berman et al., 1988, Immunol. Invest. 17:625–77), but the first three are not physiologic chemoattractants, and it seems doubtful that insulin is, because lymphocytes do not accumulate at sites of insulin injection in diabetics. Currently available lymphocyte chemotaxis assays have been reviewed (Berman et al., 1988, Immunol. Invest. 17:625–77). The most widely used is the Boyden Chamber assay, in which a microporous membrane divides two chambers, the lower containing the test chemoattractant and the upper containing the cells, e.g. lymphocytes. The microporous membrane is commonly nitrocellulose or polycarbonate, and may be coated with a protein such as collagen. The distance of migration into the filter, the number of cells crossing the filter that remain adherent to the undersurface, or the number of cells that accumulate in the lower chamber may be counted.

3. SUMMARY OF THE INVENTION

The present invention relates to a novel assay for lymphocyte chemotaxis. The assay is a transendothelial assay using endothelial cells cultured on microporous filters. Lymphocyte transmigration through the filter toward a known or suspected chemoattractant is measured. Apparatuses for carrying out the assay are also provided.

The apparatuses and methods of the present invention can be used for the identification of inhibitors (e.g., antagonists) or promoters (chemoattractants) of the adhesion receptor-mediated migration of leukocytes through the endothelium (extravasation). Such inhibitors and promoters respectively inhibit and promote the inflammatory response, and thus have therapeutic utilities. The inhibitors and promoters are identified by detecting their abilities to respectively inhibit or promote the chemotaxis of lymphocytes in the assay of the invention. The assay of the invention also has diagnostic utilities for detecting a disease or disorder involving a defect in lymphocyte chemotaxis.

In a specific embodiment, the invention provides a novel lymphocyte chemoattractant, termed LCA, of molecular weight of about 14,500 ±3,000 daltons. Derivatives and analogs of LCA, and antibodies and antibody fragments thereto are also provided. The invention also relates to therapeutic uses and compositions related to the foregoing.

3.1. DEFINITIONS

As used herein, the following terms shall have the indicated meanings:

EC=endothelial cells
FITC=fluorescein isothiocyanate
fMLP=formyl-Met-Leu-Phe
HUVEC=human umbilical vein endothelial cells
IL-8=interleukin 8
mAb=monoclonal antibody
MLR=mixed lymphocyte reaction
PBL=peripheral blood lymphocytes
PBMC=peripheral blood mononuclear cells
PHA=phytohemagglutinin

4. DESCRIPTION OF THE FIGURES

FIG. 1. A conventional (A) and a transendothelial (B) chemotaxis assay. (A) Transwell® with 8 μm polycarbonate membrane plus or minus ICAM-1, fibronectin, or collagen on the filter. The conventional assay does not detect specific migration of lymphocytes, while monocytes and neutrophils migrate specifically. (B) Transwell® with endothelial cell monolayer grown on collagen-coated 8 μm filter. A transendothelial assay of the invention detects specific migration of lymphocytes; a high ratio of migration to chemoattractant is observed relative to control media (often greater than a tenfold difference). Exemplary protocol for transendothelial chemotaxis assay: (1) Grow endothelial cell monolayer on collagen-coated, 8 μm polycarbonate Transwell® filter. (2) Add lymphocytes to upper chamber, chemoattractant to bottom chamber. (3) Remove cells from bottom chamber 1 to 4 hours later and count. Alternatively, or in addition, lymphocytes may be labeled, e.g., by a fluorescent label, such that migrating cells may be quantitated by fluorescence detection methods.

Figure 2:
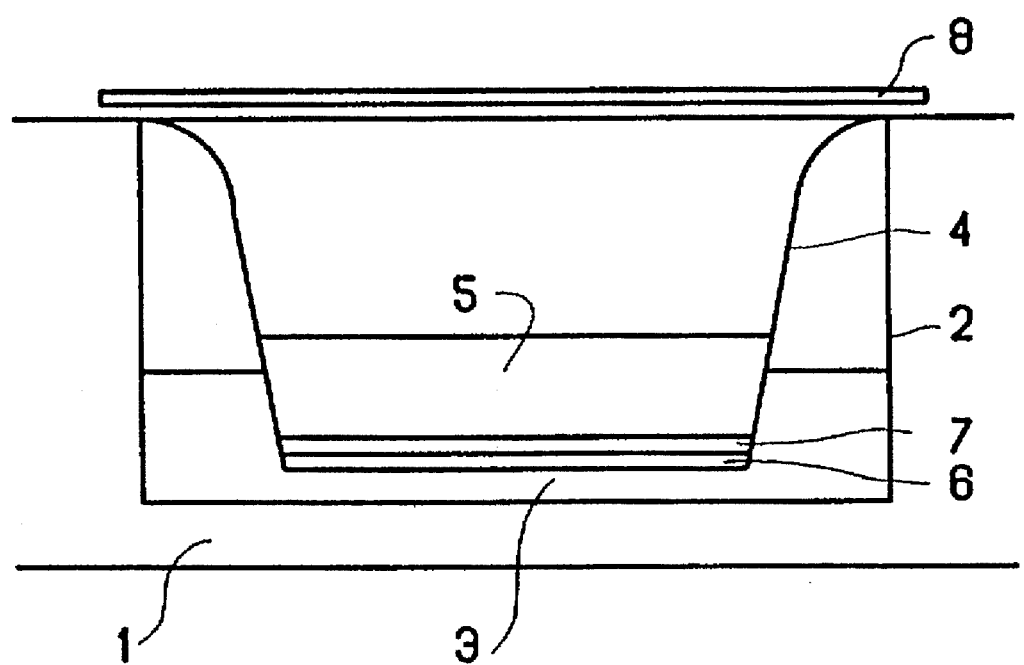

FIG. 2. Schematic diagram of an exemplary apparatus for the transendothelial chemotaxis assay of the invention.

Figure 3A:
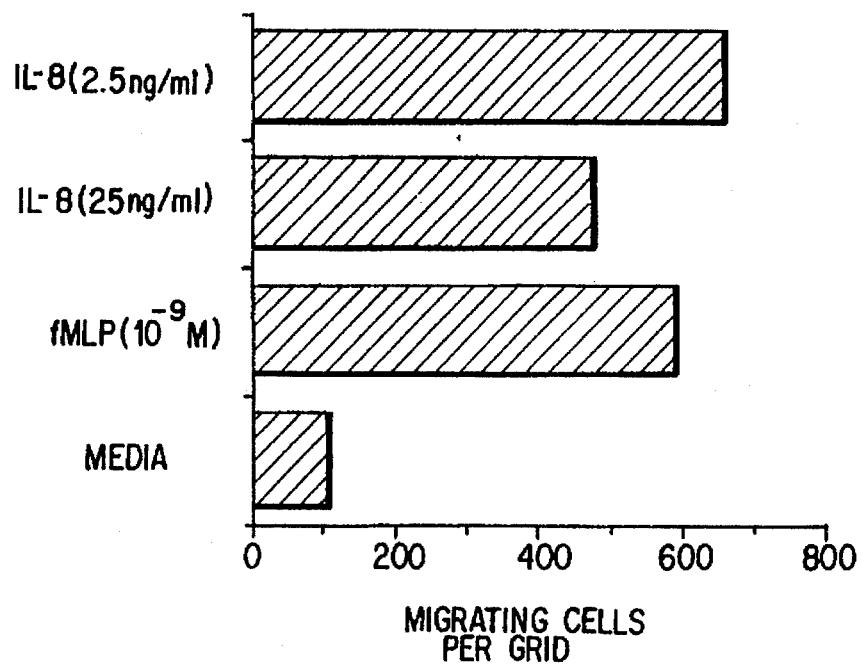

FIG. 3. Neutrophil and monocyte chemotaxis through uncoated Transwell® filters. Using the conventional chemotaxis assay, neutrophil migration to known neutrophil chemoattractants and monocyte migration to known monocyte chemoattractants was measured. A) Neutrophil chemotaxis was through 3 μm pore Transwells®. B) Monocyte chemotaxis was through 5 μm pore Transwells®. Interleukin 8 (IL-8), RANTES (both from Pepro-Tech, Rocky Hills, N.J.) and formyl-Met-Leu-Phe (fMLP) (Sigma) were used at indicated concentrations. All dilutions were in assay media which in these experiments was L-15 (Gibco) plus 1% HSA. Data are presented as average number of cells migrating per grid. Five grids per sample were counted and all samples were assayed in duplicate.

FIG. 4. Lymphocyte migration through uncoated (A) or endothelial cell-coated (B) Transwells®. A) Lymphocyte migration to mixed lymphocyte reaction (MLR) supernatant or media conditioned by phytohemagglutinin (PHA)-stimulated peripheral blood mononuclear cells (PBMC) was assayed with uncoated Transwells® using the conventional chemotaxis assay. Percent of migrating cells was calculated by counting the number of cells in the bottom chamber of each sample in a hemocytometer. The original input number of cells was also counted by hemocytometer and served as the input standard. B) Lymphocyte migration to the same supernatants was assayed using endothelial-coated Transwells® in the transendothelial chemotaxis assay. Five 10×10 grids of fluorescently labeled cells were counted for each sample and for an input cell number control. Percent of input cells migrating into the bottom chamber is presented.

Figure 5:
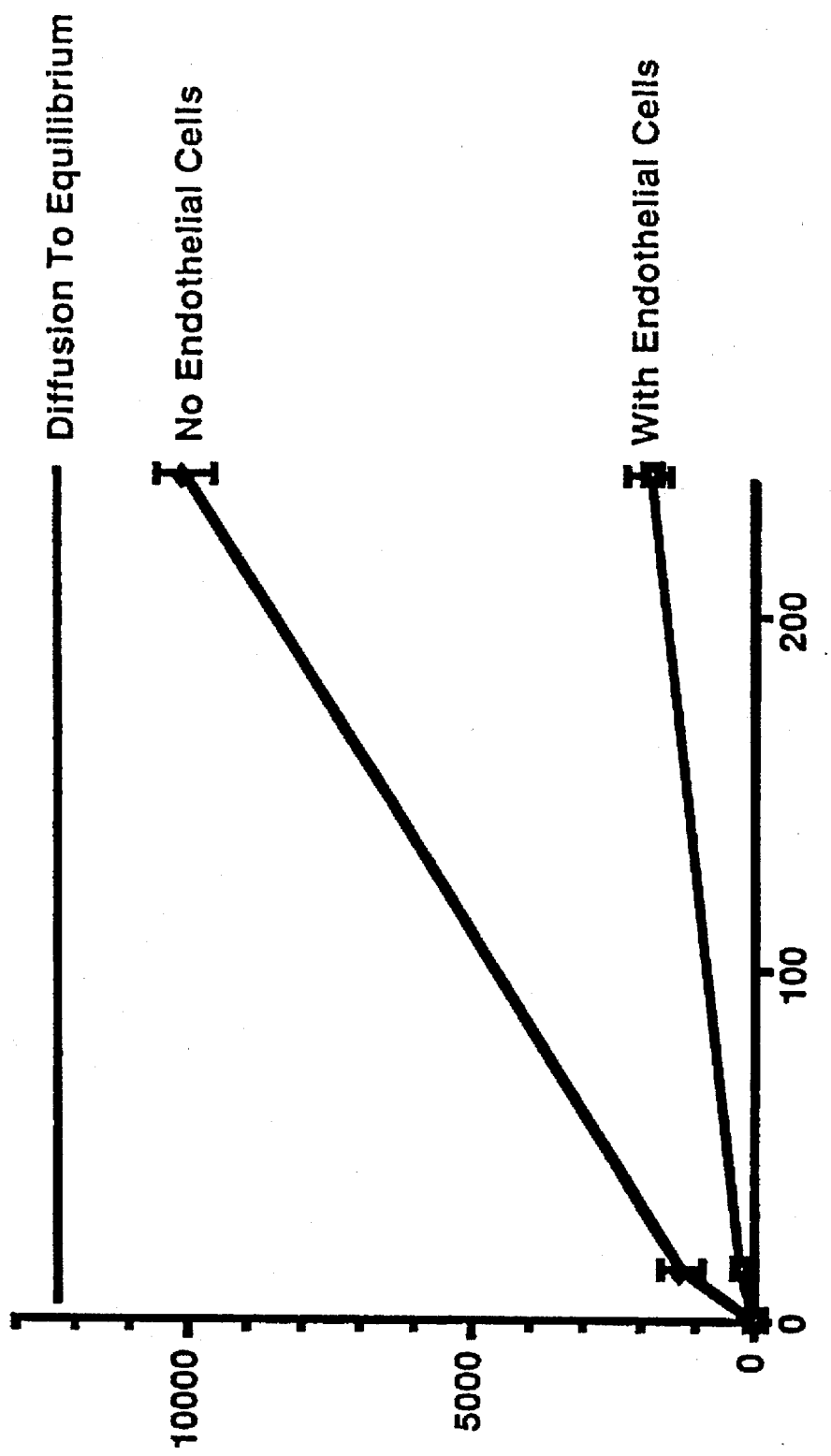

FIG. 5. Endothelial cell monolayers act as a barrier to diffusion of fluorescein isothiocyanate (FITC)-dextran. FITC-dextran (Sigma) was diluted 1:500 in assay media and 600 μl was added to three wells of a 24-well tissue culture plate; 600 μl of assay media alone was added to a fourth well. A confluent endothelial cell-coated, 8 μm Transwell® insert was placed in one FITC-dextran well and a non-endothelial cell-coated, 8 μm Transwell® insert was placed in the second FITC-dextran well. One hundred microliters of assay media was added to the top of both Transwells® and to the third FITC-dextran well, which served as the equilibrium control well. The plate was incubated at 37° C., 5% $CO_2$. After 15 min, 50 μl of media was removed from the top chamber of each Transwell® insert and from the medium and equilibrium control wells. Each sample was diluted 1:1 with assay media in a 96-well polystyrene microtiter plate (Linbro-Titertek; Flow Laboratories, McLean, Va.). Fluorescence was directly quantitated from the 96-well plate using a Pandex fluorescence concentration analyzer (Idexx Corp., Westbrook, Me.) (de Fougerolles et al., 1991, J. Exp. Med. 174:253–267). Meanwhile, 50 μl of fresh assay media was added to the top chamber of each Transwell® and control well to replace the aliquot previously removed. Samples were analyzed again after 4 hr.

Figure 6:
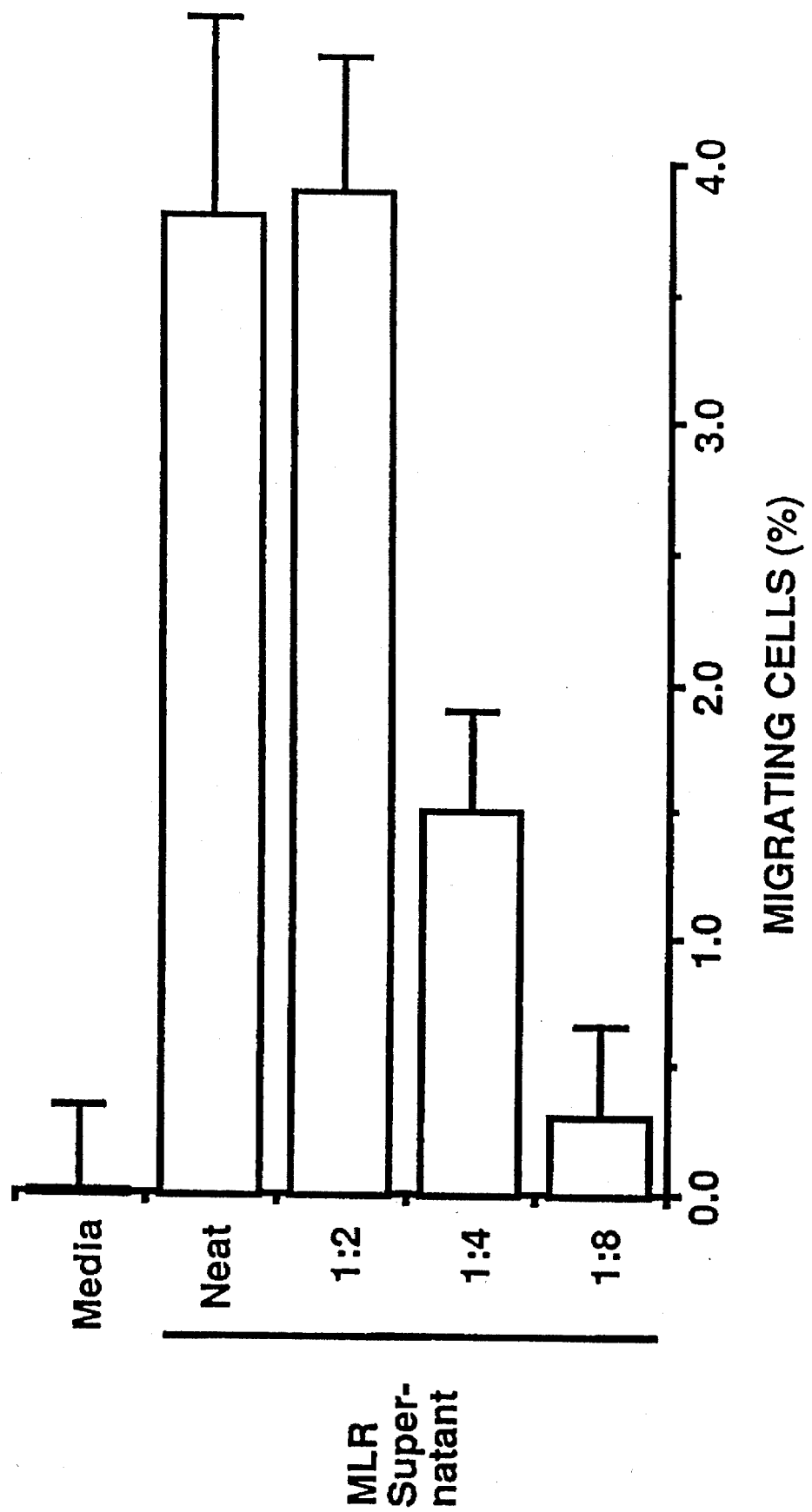

FIG. 6. Dose response of lymphocyte transendothelial chemotaxis to MLR supernatant. Chemotactic potential of MLR supernatant was assessed using the transendothelial chemotaxis assay. MLR supernatant was diluted serially in assay media and assay media was used as the media control.

Figure 7:
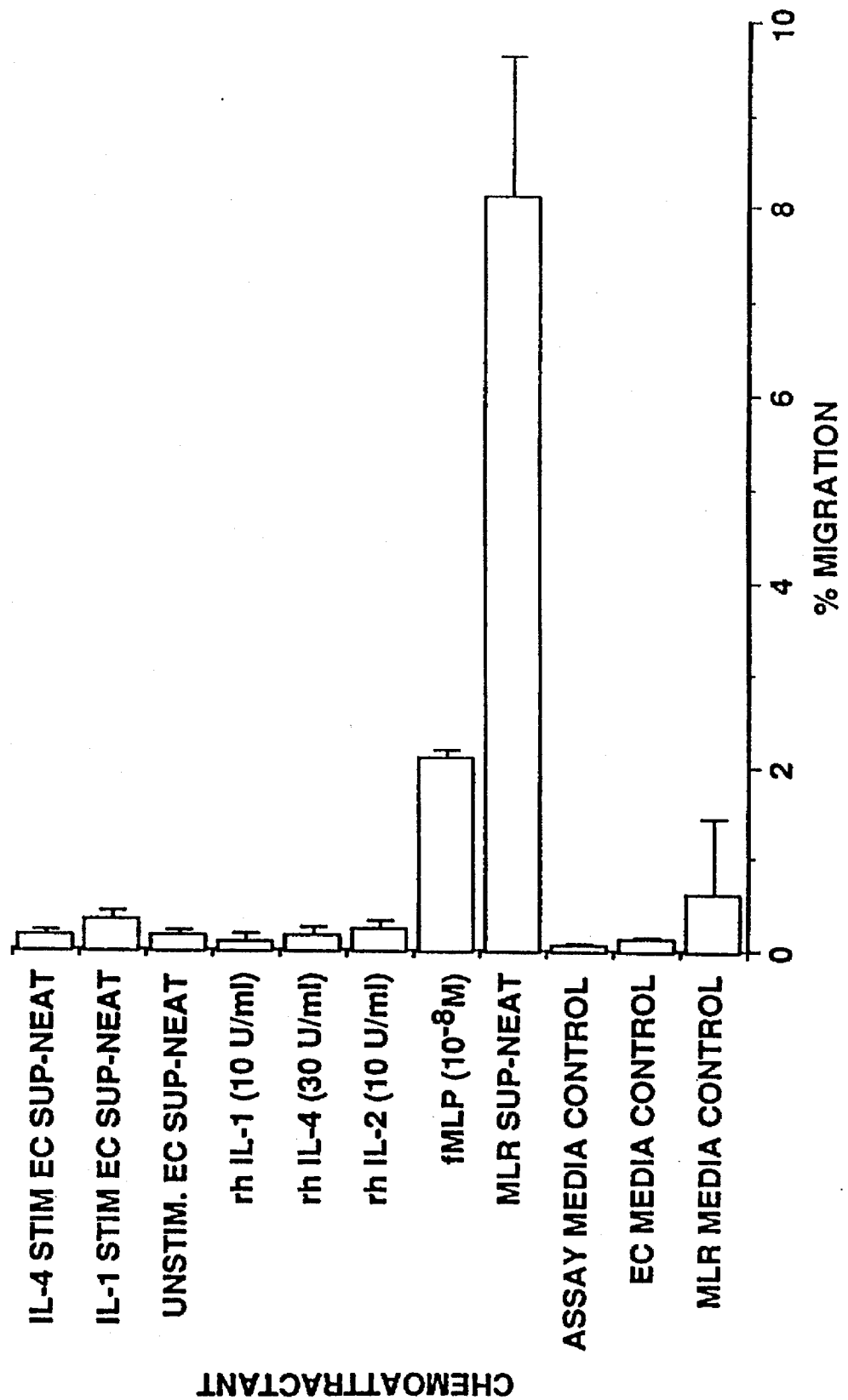

FIG. 7. Migration of peripheral blood lymphocytes (PBL) to potential chemoattractants through endothelial-coated Transwells®. The transendothelial chemotaxis assay was used to measure the chemotactic potential of cytokines or supernatant from cytokine-stimulated endothelial cells. Supernatants were harvested after 20 hr from rh-IL-1α (10 U/ml; Genzyme Corp., Cambridge, Mass.) or rh-IL-4 (30 U/ml; Genzyme)-stimulated endothelial cells. Supernatants were used undiluted in the chemotaxis assay. Recombinant human cytokines and fMLP (Sigma) were diluted, as indicated, in assay media. Endothelial cell culture media and MLR control media was as described in the text. EC: endothelial cells. Sup: Supernatant.

Figure 8:
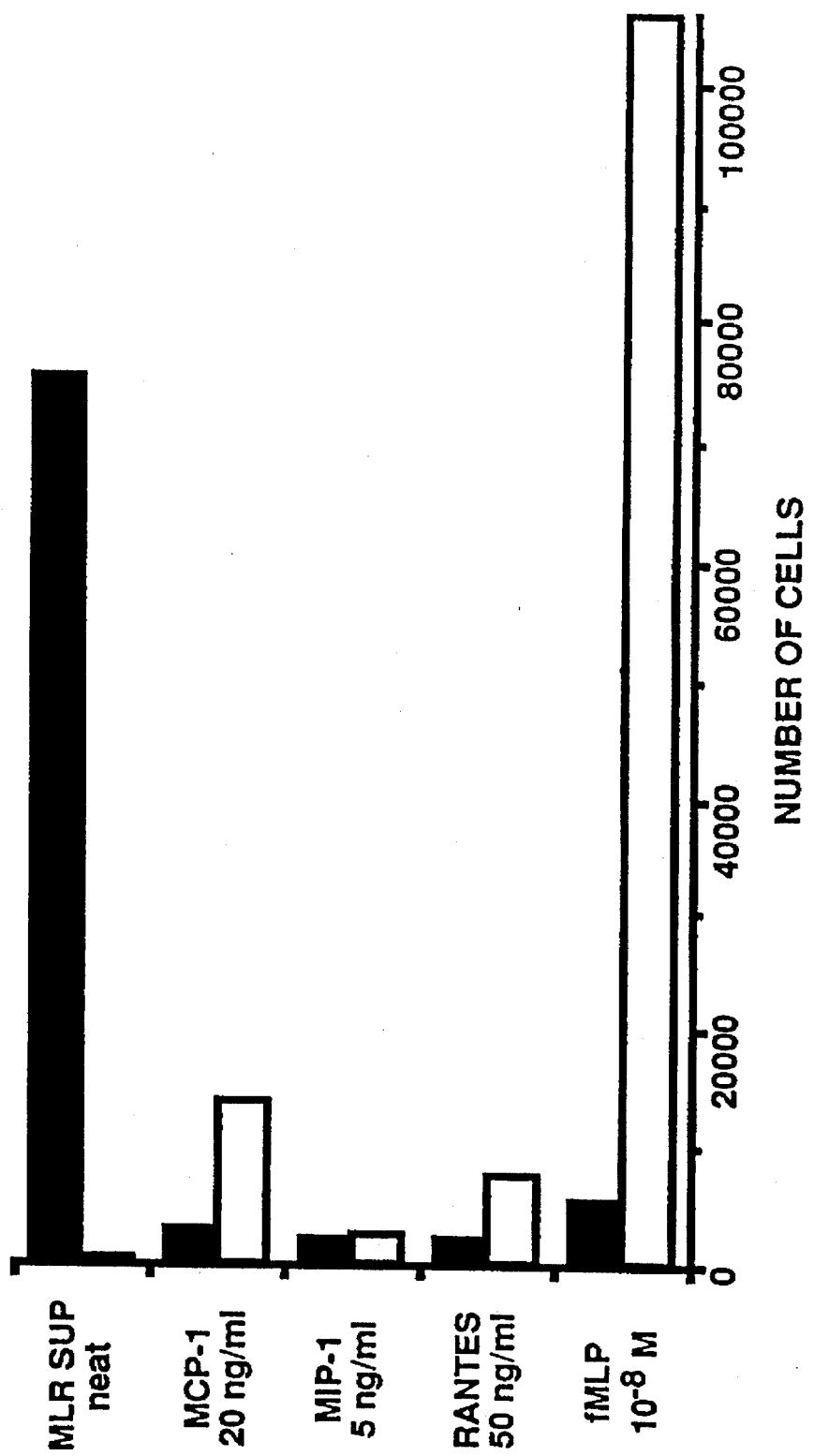

FIG. 8. $CD3^+$ T lymphocytes and $CD14^+$ monocytes among PBL migrating through endothelial-coated 8 μm Transwells®. The transendothelial chemotaxis assay was modified as follows. Endothelial cells were grown on 24.5 mm diameter, 8 μm Transwell® filters. Chemotactic factors were added to the bottom chambers in a final volume of 2 ml and 1 ml of PBL at $5\times10^6$ cells/ml was added to each top chamber. Chemotactic factors were diluted in assay media to the concentrations indicated (MCP-1 and RANTES, Pepro-Tech, Inc., Rocky Hills, N.J.; MIP-1a, R&D Systems, Minneapolis, Minn.). Following the 4 h incubation, the migrated cells in duplicate samples were harvested, washed, and resuspended in 30 μl of L-15/2% FCS. Ten microliters of each sample were added to 10 μl of monoclonal antibody (mAb) in a 96-well round bottom titertek plate. The mouse monoclonal antibodies used were X-63 (non-binding antibody control) culture supernatant, OKT3 (anti-CD3; used at 10 μg/ml), and My4 (anti-CD14; used at 10 μg/ml). After a 30 min incubation at 4° C., the cells were washed 3X and incubated with 10 μl of 1:10 diluted FITC-labeled goat anti-mouse IgG (H & L; Zymed Immunochemicals) for 30 min at 4° C. on a plate shaker. The cells were washed 3X and fixed with 2% paraformaldehyde/PBS plus EPICS Immuno-Brite fluorescent beads (Coulter Diagnostics) at a concentration of $1.3 \times 10^6$ beads/ml. Samples were analyzed using an Epics V flow cytometer. The number of positive cells for each antibody was determined by reference to the number of Immuno-Brite beads in each sample. Solid bars: $CD3^+$ cells; open bars: $CD14^+$ cells.

Figure 9:
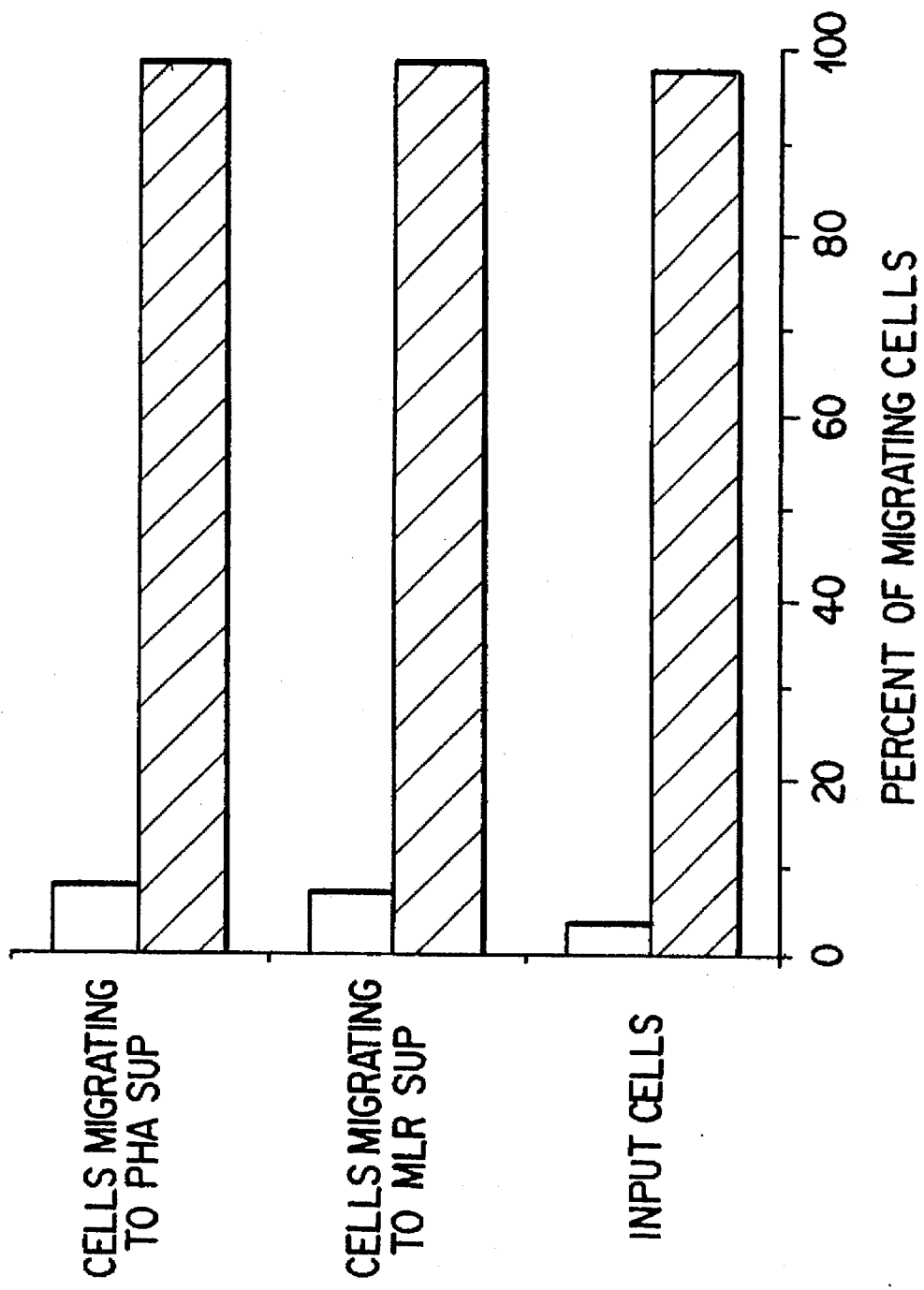

FIG. 9. $CD3^+$ lymphocytes, rather than $CD14^+$ monocytes, migrate towards MLR supernatant or supernatant from PHA-stimulated PBMC. The transendothelial chemotaxis assay was performed using the modifications described for FIG. 7. Cells migrating to MLR supernatant or supernatant from PHA-stimulated PBMC were collected from the bottom of the wells and stained with anti-CD3 or anti-CD14 antibodies, as described for FIG. 7. Solid bars: $CD3^+$ cells; open bars: $CD14^+$ cells.

Figure 10:
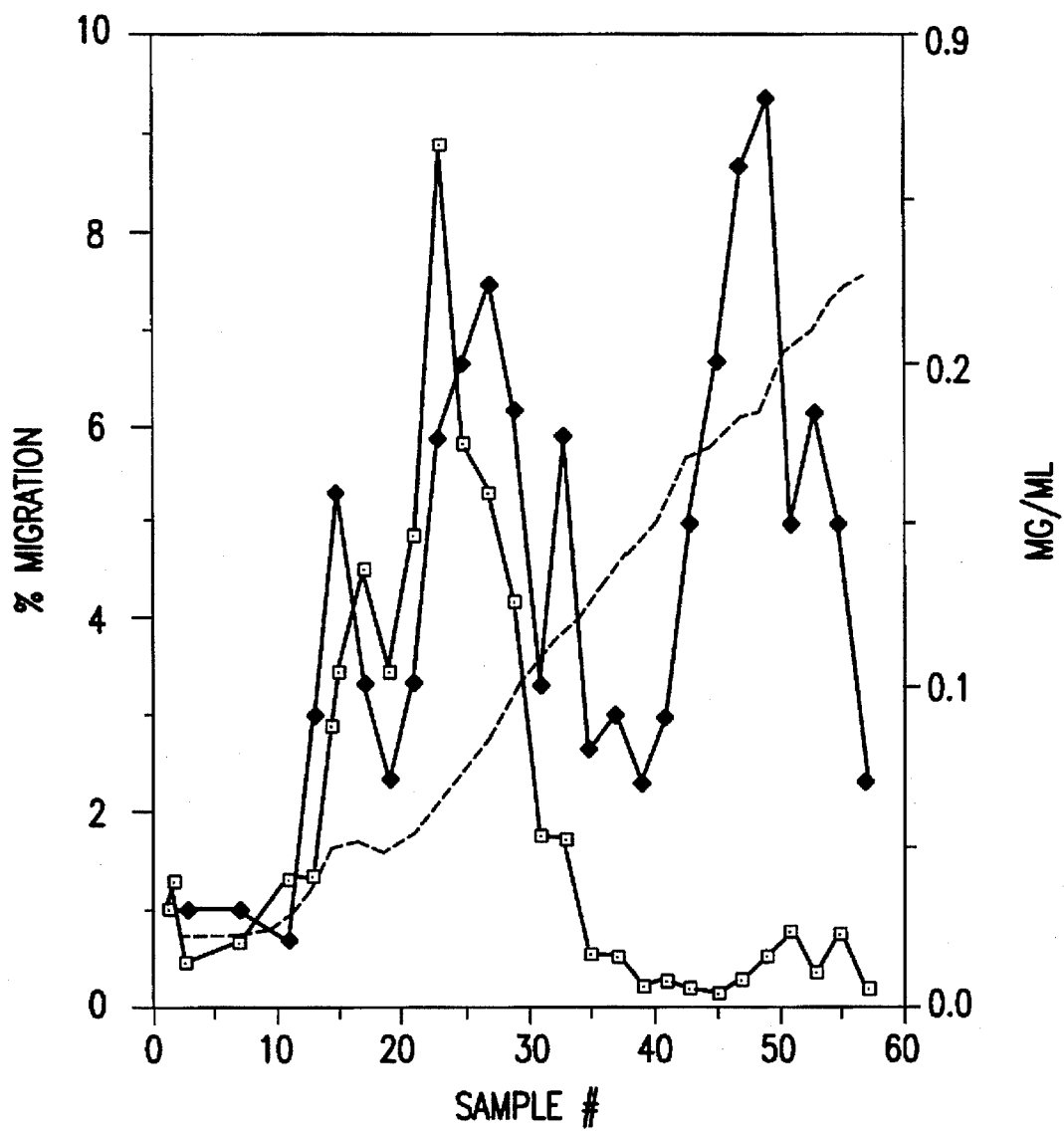

FIG. 10. Heparin-Sepharose affinity chromatography of PHA-activated PBMC supernatant. Media conditioned by PHA-stimulated PBMC was adsorbed to a 15 ml Heparin-Sepharose CL-6B column (Pharmacia) at a flow rate of 0.8 ml/min. The column was washed with 0.01 M Tris-HCl pH 7.5, 0.15 M NaCl, and protein was eluted using a 120 ml salt gradient from 0.15 M to 1.5 M NaCl in 0.01 M Tris-HCl pH 7.5. The elution flow rate was 0.23 ml/min and 2.5 ml fractions were collected. Fractions were assayed to determine protein concentration using the Bio Rad DC protein assay which is based on the traditional Lowry protein assay. Additionally, the conductivity of each fraction was measured to determine the salt concentration present in each fraction. Every third and, in some cases, every other fraction was assayed at a 1:20 dilution in the transendothelial chemotaxis assay. Percent lymphocyte migration is indicated by the untilled squares, protein concentration by the filled diamonds ($OD_{214}$), and salt (NaCl) concentration by the dotted line.

Figure 11:
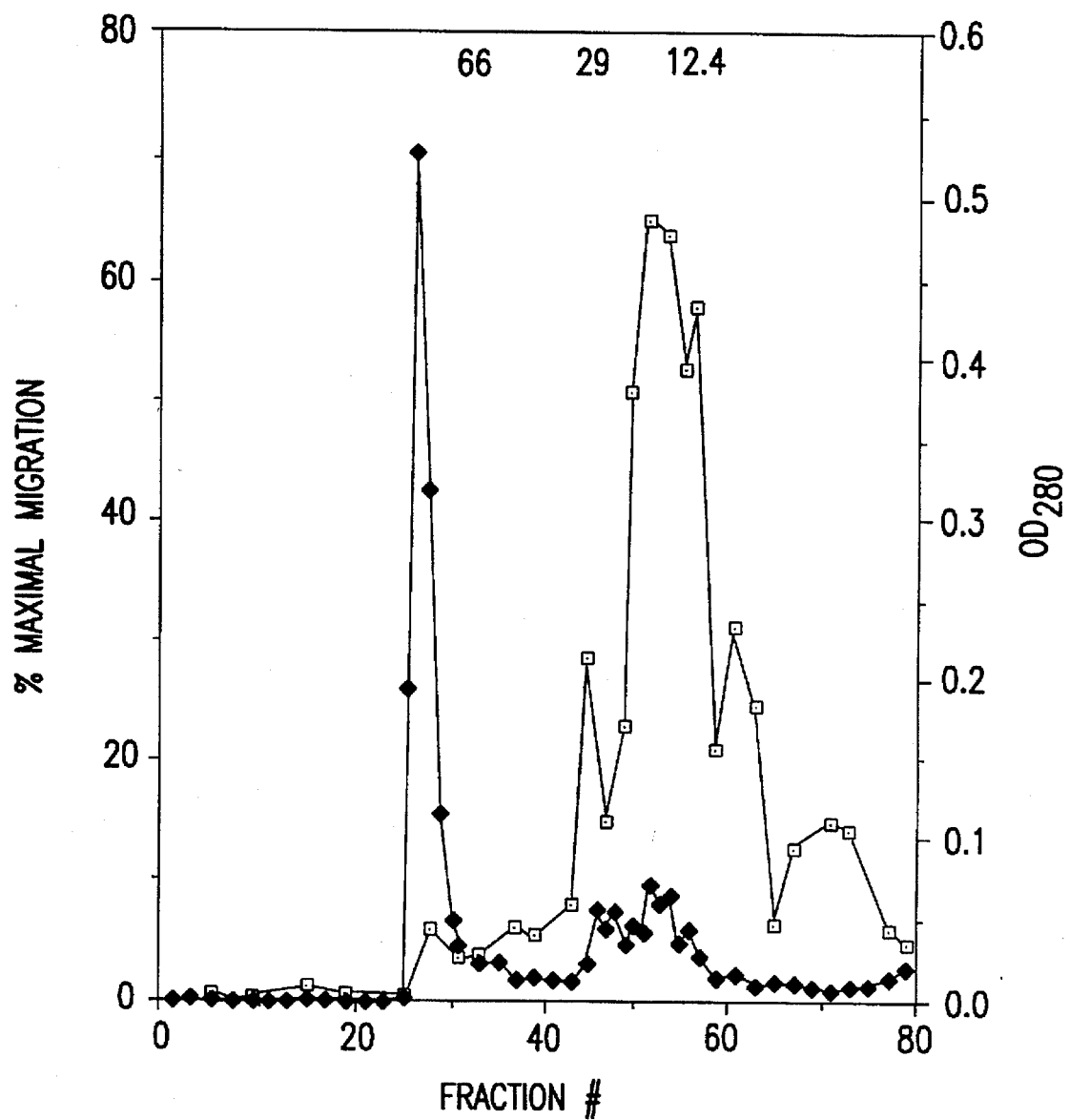

FIG. 11. Size exclusion chromatography of Heparin-Sepharose purified PHA-activated PBMC supernatant. Following Heparin-Sepharose chromatography, fractions showing lymphocyte activity in the transendothelial chemotaxis assay were pooled and concentrated 10X using Amicon centriprep concentrators with a molecular weight cut-off of 3,000 daltons. Two milliliters of concentrated sample was applied to a 125 ml Sephadex G-75 column (Pharmacia). The column was run at a flow rate of 0.07 ml/min and 1.25 ml fractions were collected. The absorbance of each fraction was monitored at 280 nm to determine protein levels. Every third fraction was assayed at a 1:4 dilution in the transendothelial chemotaxis assay. Active fractions were then re-assayed at 1:8 and 1:40 dilutions. Chemotactic activity in two different assays for 1:4 and 1:40 dilutions was normalized and presented as percent of maximal migration (1:200 of starting material) (open squares). Protein levels are shown as absorbance at 280 nm (filled diamonds). The elution positions of the molecular weight standards bovine serum albumin (66 kD), carbonic anhydrase (29 kD), and cytochrome C (12.4 kD) are indicated.

Figure 12:
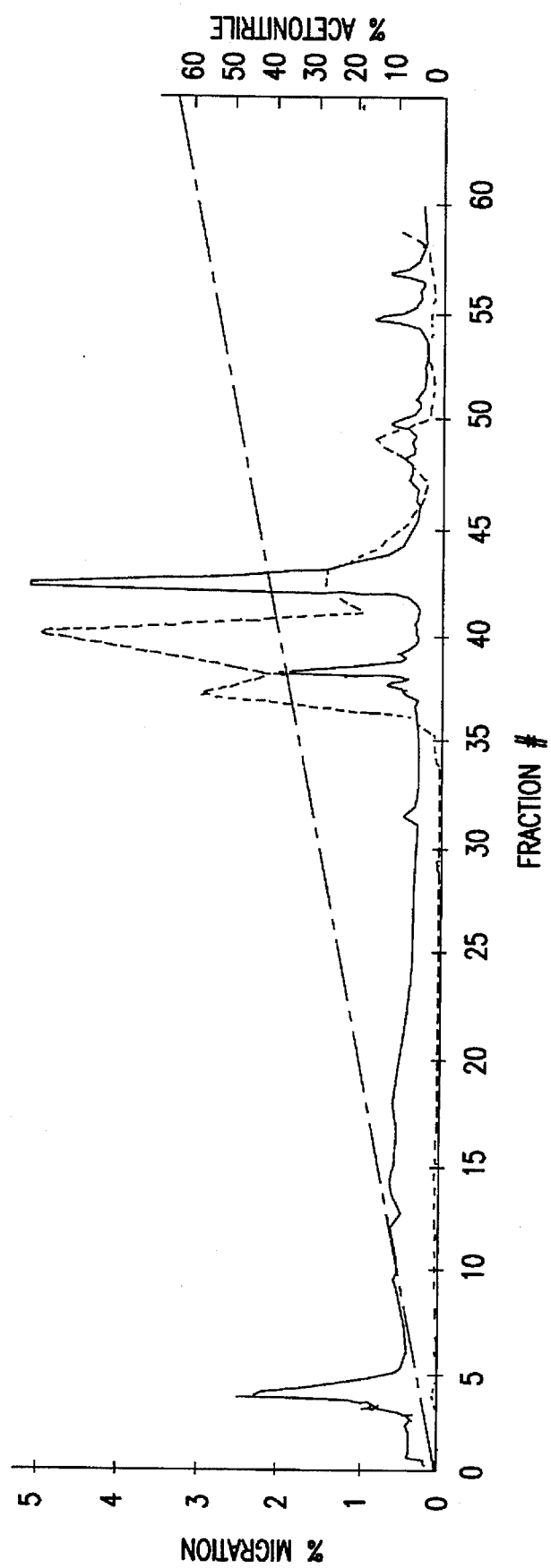

FIG. 12. Reverse phase HPLC of Heparin-Sepharose and size exclusion purified PHA-activated PBMC supernatant. Following size exclusion chromatography, fractions showing lymphocyte migratory activity in the transendothelial chemotaxis assay were pooled and concentrated approximately 20X using Amicon centriprep concentrators with a molecular weight cut-off of 3,000 daltons. Two hundred microliters of concentrated, active sample was applied to a $4.6 \times 150$ mm $C_4$ reverse phase column (5 μm: Vydac), equilibrated with a starting solvent of 0.1% trifluoroacetic acid (TFA) in water. A linear gradient was programmed, with a limit buffer of 60% (vol/vol) acetonitrile in water containing 0.1% TFA. Flow rate was 1 ml/min; 1.0 ml fractions were collected; protein levels were monitored at $A_{280}$ and $A_{214}$. Fractions 30–60, as well as selected early fractions, were assayed at a 1:4 dilution in the lymphocyte transendothelial chemotaxis assay. Percent lymphocyte migration is indicated by the dashed line; absorbance at 280 nm is indicated by the solid line, and the acetonitrile gradient is indicated by the dash/dot line.

5. DETAILED DESCRIPTION OF THE INVENTION

5.1. A TRANSENDOTHELIAL LYMPHOCYTE CHEMOTAXIS ASSAY

We have developed a novel assay for lymphocyte chemotaxis. The assay is a transendothelial assay that allows quantitation of cells accumulating in the chamber containing the chemoattractant, has a high signal-to-noise ratio, is highly reliable, and provides a method of screening for and purification of novel chemoattractants (FIG. 1). The assay has utility for identification and monitoring of purification of chemoattractants, and in screening for antagonists of lymphocyte chemoattraction (chemotaxis inhibitors).

The invention is based in part on our discovery that lymphocytes behave differently than monocytes and neutrophils in chemotaxis chambers. Neutrophils migrate vigorously to the formylpeptide f-Met-Leu-Phe and IL-8, and monocytes respond well to f-Met-Leu-Phe and much less so to RANTES. The response is readily measurable by counting the number of cells that appear in the bottom chamber. By contrast, only a small percentage of lymphocytes migrate through polycarbonate filters with 5 μm pores, whereas a high percentage of cells (30–40%) migrate or fall through 8 μm pores, whether or not chemoattractant is added. The same 8 μm filters in the same geometry are used by other investigators to assay for chemotaxis by counting the number of cells that migrate through the filter and stick to the underside (Schall et al., 1990, Nature 347:669–671). However, our results show that these must be numerically a very small percentage of the cells that fall or migrate through the filter. Therefore, these may be assays of sticking rather than chemotaxis.

We have developed an excellent lymphocyte chemotaxis assay by culturing endothelium on microporous filters coated with collagen or fibronectin, and assaying lymphocyte transmigration toward chemoattractants.

The results with the transendothelial chemotaxis assays of the invention are in sharp contrast to assays with microporous membranes alone (see Section 6). The transendothelial chemotaxis assay system accurately recapitulates lymphocyte emigration from blood vessels toward chemoattractants in vivo, in which cells migrate through endothelium and basement membrane into tissues. We thus term these assay chambers a type of "artificial vessel construct."

Chemokinesis is defined as stimulated motility that is random in direction, whereas chemotaxis is directional towards the stimulus. The activity we have defined is directional, because "checkerboard assays" (see Zigmond and Hirsch, 1973, J. Exp. Med. 137:387–410) show that lymphocytes migrate when chemoattractant is present in the bottom chamber and not in the top, but that migration falls off as chemoattractant is added to the top chamber (see Section 6).

The artificial vessel construct for use in the lymphocyte chemotaxis assay of the invention comprises a filter on which an endothelial cell monolayer consisting of living (e.g., not fixed) cells is situated. The filter is a microporous filter, of pore size in the range of about 3–8 microns, preferably 5–8 microns. In specific embodiments, the filter pore size is in the range of 4–7 microns, or is 5 or 8 microns. The filter is polycarbonate, nitrocellulose, or other polymer, and is preferably polycarbonate.

To produce an artificial vessel construct of the invention, a composition such as one comprising fibronectin or collagen is placed on the filter so as to coat the filter's surface, in order to allow attachment of endothelial cells to the filter. In a preferred embodiment, type I collagen is applied to the filter. Fibronectin and collagen can be obtained and/or purified by use of any methods known in the art. Compositions comprising fibronectin or collagen are also commercially available. For example, fibronectin can be purchased from Telios, Inc. (La Jolla, Calif.); type I collagen can be purchased from Organogenesis, Inc. (Canton, Mass.).

The filter coated with the fibronectin or collagen composition is preferably then incubated for a short time after coating (e.g., at least about one-half hour at 37° C.).

An endothelial cell monolayer is then grown on the surface of the filter coated with the fibronectin or collagen. This is done by methods known in the art. In particular, a composition comprising endothelial cells is added to the coated filter surface, and then cultured under standard growth conditions. Preferably, endothelial cell monolayers that have reached confluence are employed in the assay of the invention; such confluent monolayers prevent media components from diffusing too quickly across the filter during the assay (see infra). Endothelial cells suitable for use can be obtained from any in vivo source, including but not limited to tissue comprising any vein or artery or microvascular endothelium. Umbilical vein is the most accessible source. Human umbilical vein endothelial cells (HUVECs) are most preferred, and are commercially available (Clonetics Corp., San Diego, Calif.). Unstimulated endothelium is preferred for use, since stimulated endothelium has yielded higher background levels in the chemotaxis assay of the invention. Procedures for harvesting and culturing endothelial cells are known in the art. For example, HUVECs can be harvested as described by Wheeler et al. (1988, J. Clin. Investigation 82:1211) and cultured as described by Luscinskas et al. (1991, J. Immunol. 146:1617–1625). The endothelial cells are mammalian, including cows, dogs, pigs, and are most preferably human. Human endothelial cells are strongly preferred for use in assaying human lymphocyte chemotaxis.

The lymphocyte chemotaxis assay of the invention is carried out by detecting migration of lymphocytes through the filter containing the EC monolayer on a first surface, wherein migration occurs in the direction from the first surface of the filter through to the opposite, second surface, wherein a known or suspected chemoattractant is situated below the second surface at increased levels relative to the levels present above the first surface such that the direction of migration is toward the chemoattractant. In a particular embodiment, the filter with the EC monolayer thereon is situated in between two chambers (a "first chamber" and a "second chamber") so as to separate one chamber from the other. The chambers can be formed from various solid phase materials, including but not limited to plastic, glass, quartz, polystyrene, polypropylene, and is most preferably plastic. Preferably, the chambers are separately detachable from the filter, so as to facilitate counting of cells present thereon after chemotaxis has occurred (see infra). Optionally, each chamber has one or more ports or inlet means or other openings for injection of solutions. In a preferred embodiment, a Transwell® culture insert such as the insert commercially available from Costar (Cambridge, Mass.; Transwell® 3422) is employed.

A schematic diagram of an exemplary chemotaxis assay apparatus of the invention is shown in FIG. 2. A cluster plate 1 contains a plurality of assay wells, one of which is depicted. The assay well consists of a bottom chamber 2 filled with fluid 3, into which is placed a removable upper chamber 4 containing fluid 5 in which lymphocytes are present. A microporous filter 6 is situated at the interface between the top and bottom chambers, on the upper surface of which filter is a confluent endothelial cell monolayer 7 grown thereon. A cover 8 for the assay well is also provided.

In a specific embodiment, an apparatus of the invention comprises: (a) a filter with a pore size in the range of 4–7 microns; (b) an endothelial cell monolayer grown on the upper surface of said filter; (c) a first chamber having an opening communicating with said endothelial cell monolayer; and (d) a second chamber having an opening communicating with the lower surface of the filter. Preferably, the opening of the second chamber is substantially congruent with the opening of the first chamber.

To one of the chambers of the apparatus ("the first chamber") is added a composition containing lymphocytes. The composition is preferably a composition that is enriched for lymphocytes and substantially depleted of non-lymphocytic blood cells. In one embodiment, the composition contains a cell population that is greater than 85%, 90%, or most preferably, 95% lymphocytes. Lymphocyte enrichment is carried out by any method known in the art. For example and not by way of limitation, whole blood is collected, an anti-coagulent such as acid citrate is added, peripheral blood mononuclear cells are obtained therefrom by dextran sedimentation and centrifugation on a Ficoll Hypaque cushion, and lymphocytes are enriched and monocytes depleted by collecting nonadherent cells after serial incubations on plastic dishes.

In a specific embodiment (see infra) in which migrating lymphocytes are detected or measured by detecting and/or quantitating a label appearing in the other chamber of the apparatus ("the second chamber"), the cells are labeled before placing them in the first chamber. This can be accomplished by any of various methods known in the art, e.g., by fluorescent labeling of the cells, enzymatic labeling (e.g., via an enzyme-tagged antibody to a lymphocyte cell surface marker), etc. In a preferred aspect, cells are fluorescently labeled with fluorescein or a derivative thereof such as 2',7'-bis-(2-carboxyethyl)-5(and 6)-carboxyfluorescein (BCECF) or calcein (Molecular Probes, Eugene, Oreg.).

Simultaneously, or shortly before or after addition of the cellular composition to the first chamber, a composition comprising or suspected of comprising a lymphocyte chemoattractant is placed inside the second chamber. A "test molecule" as used herein refers to a molecule being tested for the desired activity in promoting or inhibiting lymphocyte chemotaxis, as the case may be (see Sections 5.2 and 5.3, infra). A test molecule being tested for its ability to inhibit lymphocyte chemotaxis is preferably placed in the first chamber along with the composition containing lymphocytes when conducting the chemotaxis assay. A test molecule which is being tested for its ability to promote lymphocyte chemotaxis is preferably placed instead of, or (less preferably) in addition to, a known chemoattractant in the second chamber when conducting the chemotaxis assay.

The filter should be situated so as to be in contact with both fluid containing the cellular composition in the first chamber, and fluid containing the chemoattractant/test molecule in the second chamber. Except for added test molecules or cells as stated above, the fluids in the first and second chambers are preferably the same or substantially similar. Additionally, the fluids in the first and second chambers preferably comprise cell culture media, for example, RPMI 1640 (e.g., from Gibco) (or L15) plus M199 (e.g., Gibco) (preferably in a 1:1 ratio). It is important to add some protein such as human serum albumin (HSA), bovine serum albumin (BSA), or fetal calf serum (FCS) to the fluid in both the first and second chambers, to a final concentration in the range of 0.25–1%; the same protein need not be present in both chambers. (Although not intending to be bound by any mechanism, Applicants believe that such proteins aid in the assay of the invention by increasing protein stability and inhibiting nonspecific sticking of cells.) Dilutions of test molecules or chemoattractants are preferably carried out in fluid identical to that present in the chamber to which said molecule or chemoattractant is to be added.

After placement of the cellular composition and chemoattractant composition in the first and second chambers, respectively, the apparatus is incubated to allow any chemotaxis of lymphocytes to take place. Incubation is carried out for a time period in the range of about 3–6 hours, and is most preferably done for 4 hours at about 37° C. In an embodiment where RPM11640 medium is employed in one or more of the chambers, incubation is preferably done at 5 % $CO_2$; in an embodiment where L15 medium is employed, incubation at 5% $CO_2$ is not necessary since L15 can be used in room air.

Following incubation, chemotaxis is detected and/or measured. This is done by detecting and/or measuring the lymphocytes that are present in the second chamber (by virtue of having migrating through the coated filter connecting the first chamber to the second chamber). The detection and/or measurement can be done by any method known in the art. For example, where the cells placed in the top chamber were labeled, the label can be detected and/or measured; for example, cells in the bottom chamber can be counted by fluorescent microscopy or quantitated in a Pandex fluorescence concentration analyzer. Alternatively, the cells can be retrieved from the second chamber and counted directly under the microscope. Many methods are available to the skilled artisan. Data can be expressed by any convenient method, e.g., as absolute number of cells or as percentage of input cells migrating into the second chamber.

In a preferred aspect, chemotaxis is detected or measured by determining data relative to a control or background level of migration into the second chamber measured in which no chemoattractant or test molecule is placed in the second chamber. An increased number of cells (or percentage of input cells, as the case may be) in the second chamber relative to the background level indicates chemotaxis (or chemokinesis) has occurred. [Chemokinesis can be distinguished from chemotaxis, e.g., by a checkerboard analysis (Zigmond and Hirsch, 1973, J. Exp. Med. 137:387–410)].

5.2. IDENTIFICATION OF PROMOTERS OF LYMPHOCYTE CHEMOTAXIS

Use of transendothelial lymphocyte chemotaxis assay provides a method of screening for promoters of lymphocyte chemotaxis, e.g., lymphocyte chemoattractants. Positive lymphocyte chemotaxis, as detected in the assay, indicates the presence of a lymphocyte chemoattractant.

A lymphocyte chemoattractant is detected by its ability to promote lymphocyte chemotaxis in an assay of the invention, where lymphocyte chemotaxis, in the absence of the chemoattractant molecule, was previously lacking or at decreased levels. Thus, a sample comprising a "test molecule" suspected of having chemoattractant activity is placed in the second chamber of an apparatus of the invention, in a fluid, and an increase in lymphocyte chemotaxis relative to levels of lymphocyte chemotaxis in the absence of the test molecule, or to background levels (baseline levels, with no chemoattractant), indicates that the molecule is a lymphocyte chemoattractant. Molecules to be tested for chemoattractive ability can be any of interest. In a specific embodiment, the chemotaxis assay of the invention can be used to screen natural product or synthetic chemical libraries (e.g., peptide libraries) to identify novel lymphocyte chemoattractants.

Use of a transendothelial lymphocyte chemotaxis assay of the invention also provides a method of monitoring the purification of a chemoattractant (or, alternatively, of a chemoattraction inhibitor), by observing its activity in the chemotaxis assay at various stages of the purification process. For example, in purifying a chemoattractant, increased purity of a functionally active chemoattractant is confirmed by observing increased chemotaxis in response to samples of the chemoattractant relative to the chemotaxis observed in response to samples of the chemoattractant from earlier stages of the purification process.

5.2.1. LCA, A NOVEL LYMPHOCYTE CHEMOATTRACTANT

In another embodiment, the invention provides a novel substantially purified lymphocyte chemoattractant of molecular weight of about 14,500±3,000 daltons (hereinafter termed the "LCA," for "lymphocyte chemoattractant"). LCA was identified as present in medium conditioned by PHA-activated PBMC, by detecting its chemotactic activity in the assay of lymphocyte chemotaxis provided by the invention. LCA is distinct from previously reported cytokines and lymphokines, some of which have been reported to have lymphocyte chemoattractive activity, but which are without effect in our assay. It is also distinct from a lymphocyte chemoattractant described by Center and coworkers (Center and Cruikshank, 1982, J. Immunol. 128:2563–68; Cruikshank and Center, 1982, J. Immunol. 128:2569; Cruikshank et al., 1991, J. Immunol. 146:2928–34; Berman et al., 1988, Immunol. Invest. 17:625–77) by several criteria. First, it is distinct in molecular weight as determined by size exclusion chromatography. The factor of Center et al is 56,000 $M_r$, whereas LCA is of about 14,500 $M_r$. Secondly, that of Center et al. attracts only $CD4^+$ T lymphocytes, whereas LCA attracts both $CD4^+$ and $CD8^+$ T lymphocytes. LCA has chemoattractive activity for memory ($CD45RO^+$) but not naive ($CD45RA^+$) T cells.

LCA is preferably obtained from medium conditioned by activated PBMC, preferably PHA-activated PBMC. Purification can be carried out by standard methods known in the art, including but not limited to chromatography (e.g., ion exchange, affinity, and sizing column chromatography), centrifugation, differential solubility, or by any other standard technique for the purification of proteins. In a preferred aspect, LCA is purified by methods known in the art, such as Heparin-Sepharose affinity chromatography followed by size exclusion chromatography and reverse-phase high pressure liquid chromatography, until the chemoattractant is homogenous as determined by SDS-PAGE.

Various assays to monitor purity and confirm identity of LCA can be used; in particular, the lymphocyte chemotaxis assay of the invention is used. Alternatively, or additionally, assays which can be used include but are not limited to those measuring the stimulation by chemoattractants of lymphocyte adhesion to integrin ligands such as ICAM-1, 2, or 3, VCAM-1, fibronectin, laminin, or collagen, immobilized on a substrate. Alternatively, adhesion to fibroblast or endothelial cell monolayers, or after removal of these cells, the underlying extracellular matrix, is measured. Chemoattractants may be mixed with the incubation medium. Alternatively, the chemoattractant is preincubated with proteoglycans, heparin, or chondroitin sulfate coimmobilized with the purified integrin ligands, or with the cells or extracellular matrix, and after washing, a second incubation with lymphocytes carried out. The number of bound lymphocytes is then determined with methods known in the art such as fluorescent dyes.

The purified LCA can be subjected to amino acid sequencing, either of the amino terminus or of peptide fragments, to determine its amino acid sequence. Chemical synthesis, e.g. by use of an automated peptide synthesizer, can then be used to obtain purified LCA.

The chemoattractant we have characterized, LCA, has therapeutic utility as described infra, e.g., for administration in the bloodstream to antagonize lymphocyte accumulation at sites of inflammation and inflammatory disease.

5.2.2. DERIVATIVES AND ANALOGS OF LCA

The invention further provides derivatives (including but not limited to fragments) and analogs of LCA.

The production and use of derivatives and analogs related to LCA are within the scope of the present invention. In a specific embodiment, the derivative or analog is functionally active, i.e., capable of exhibiting one or more functional activities associated with the full-length, wild-type LCA protein. Such functional activities include but are not limited to chemoattraction, antigenicity [ability to bind (or compete with an LCA protein for binding) to an anti-LCA antibody], immunogenicity (ability to generate antibody which binds to LCA), and ability to bind (or compete with LCA for binding) to its receptor on a cell (particularly, on a lymphocyte). As one example, such derivatives or analogs which have the desired immunogenicity or antigenicity can be used, for example, in diagnostic immunoassays as described in Section 5.7. Molecules which retain, lack, or inhibit, a desired LCA property, e.g., chemoattraction, binding to its receptor protein, can be used therapeutically as inducers, or inhibitors, as the case may be, of such property and/or its physiological correlates. Derivatives or analogs of LCA can be tested for the desired activity by procedures known in the art, including but not limited to the assays described infra in Section 5.2.3.

In particular, LCA derivatives can be made by altering LCA sequences by substitutions, additions or deletions that provide for functionally equivalent molecules. LCA derivatives of the invention include, but are not limited to, those containing, as a primary amino acid sequence, all or part of the amino acid sequence of a LCA protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a LCA protein consisting of at least five amino acids of the LCA protein is provided. In other embodiments, the fragment consists of at least 10, 15, 25, 50, or 100 amino acids of the LCA protein.

Derivatives or analogs of LCA include but are not limited to those peptides which are substantially homologous (e.g., greater than 70% identity) to a LCA or a fragment thereof. In specific embodiments, fragments of LCA are at least 15, 30, or 50 amino acids thereof.

The LCA derivatives and analogs of the invention can be produced by various methods known in the art. Also provided by the invention are LCA fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, etc.

In addition, analogs and derivatives of LCA proteins can be chemically synthesized. For example, a peptide corresponding to a portion of LCA which mediates the desired activity in vitro or in vivo, can be synthesized by use of a peptide synthesizer. Furthermore, if desired, nonclassical amino acids or chemical amino acid analogs can be introduced as a substitution or addition into the human LCA protein sequence. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

In a specific embodiment, the LCA derivative is a chimeric, or fusion, protein comprising LCA or a fragment thereof (preferably consisting of at least 5 amino acids of the LCA protein) joined at its amino or carboxy-terminus via a peptide bond to an amino acid sequence of a different protein. In one embodiment, such a chimeric product may be made by protein synthetic techniques, e.g., by use of a peptide synthesizer.

5.2.3. ASSAYS OF LCA AND ITS DERIVATIVES AND ANALOGS

The functional activity of LCA, and its derivatives and analogs (as well as other chemoattractants identified by the assay of the invention and derivatives and analogs thereof), can be assayed by various methods.

In a preferred embodiment, where one is assaying for chemoattraction or inhibition thereof, the transendothelial lymphocyte chemotaxis assay of the invention is employed. In another embodiment, where one is assaying for the ability to bind or compete with a wild-type LCA protein for binding to anti-LCA protein antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention.

The ability to bind to another protein (e.g., a LCA receptor) can be demonstrated by in vitro binding assays, noncompetitive or competitive, by methods known in the art.

In another embodiment, physiological correlates of LCA administration to cells can be assayed.

Other methods will be known to the skilled artisan and are within the scope of the invention.

5.3. IDENTIFICATION OF INHIBITORS OF LYMPHOCYTE CHEMOTAXIS

The assays of the invention can be used to identify an inhibitor of lymphocyte chemotaxis, e.g., an antagonist of lymphocyte chemotaxis. Such an inhibitor can be used therapeutically, e.g., as an inhibitor of the inflammatory response by inhibition of lymphocyte extravasation.

Such an inhibitor is detected by its ability to inhibit lymphocyte chemotaxis in an assay of the invention. Thus, in a preferred aspect, such an inhibitor is detected by carrying out the assay of the invention in which: (i) a sample comprising a compound with known lymphocyte chemoattractant activity is placed in the second chamber of the assay apparatus; (ii) a first composition comprising a test molecule suspected of having inhibitory activity is placed in the first chamber; and (iii) a second composition comprising lymphocytes is placed in the first chamber. A decrease in lymphocyte chemotaxis relative to the chemotaxis observed under the same conditions except in the absence of the test molecule, indicates that the molecule is an inhibitor of lymphocyte chemotaxis (and thus has utility as an inhibitor of lymphocyte extravasation).

Molecules to be tested for inhibitory activity can be any of interest, including but not limited to antibodies (preferably monoclonal, most preferably human or humanized monoclonal, or antigen-binding domains thereof), chemoattractant receptors, integrins, integrin binding partners, peptide antagonists and peptidomimetics, etc. In a specific embodiment, the assay can be used to screen natural product or synthetic chemical libraries (e.g., peptide libraries) to identify antagonists of lymphocyte chemotaxis.

5.4. GENERATION AND USE OF ANTIBODIES TO LYMPHOCYTE CHEMOATTRACTANTS AND CHEMOTAXIS INHIBITORS

According to the invention, the lymphocyte chemoattractants, lymphocyte chemotaxis inhibitors, and derivatives and analogs thereof, provided by the invention, or cells expressing the foregoing may be used as an immunogen to generate antibodies which recognize such an immunogen. Such antibodies include but are not limited to polyclonal, monoclonal, chimeric, single chain, Fab fragments, and an Fab expression library.

Various procedures known in the art may be used for the production of polyclonal antibodies. In a particular embodiment, rabbit polyclonal antibodies which bind the molecule of the invention can be obtained. For the production of antibody, various host animals can be immunized by injection with the native molecule, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes or portions thereof (e.g., hypervariable regions) from a mouse antibody molecule specific for the desired molecule together with genes from a human antibody molecule (e.g., the constant regions) of appropriate biological activity can be used; such antibodies are within the scope of this invention.

According to the invention, techniques described for the production of single chain antibodies (U.S. Pat. No. 4,946,778) can be adapted to produce single chain antibodies. An additional embodiment of the invention utilizes the techniques described for the construction of Fab expression libraries (Huse et at., 1989, Science 246:1275–1281) to allow rapid and easy identification of monoclonal Fab fragments with the desired specificity for the molecules, derivatives, or analogs of the invention.

Antibody fragments which contain the idiotype (binding domain) of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g. ELISA (enzyme-linked immunosorbent assay). For example, to select antibodies which recognize a specific domain of a molecule, one may assay generated hybridomas for a product which binds to a fragment of the molecule containing such domain.

The foregoing antibodies can be used therapeutically, as well as in methods known in the art relating to the measurement, localization and activity of the molecules which they recognize, e.g., for imaging these molecules, measuring levels thereof in appropriate physiological samples by immunoassay, etc.

In a specific embodiment, antibodies to LCA are produced. In a particular embodiment, such antibodies are neutralizing (i.e., block the chemoattractive action of LCA). Such antibodies can be identified by various assays, for example, by detecting the ability of the antibody to inhibit lymphocyte chemotaxis toward LCA, when present with LCA in the transendothelial chemotaxis assay of the invention. In another embodiment, such a neutralizing anti-LCA antibody is identified by detecting its ability to block binding of LCA to its lymphocyte cell-surface receptor.

5.5. THERAPEUTIC USES OF LYMPHOCYTE CHEMOATTRACTANTS, CHEMOTAXIS INHIBITORS, AND ANTIBODIES TO THE FOREGOING

The lymphocyte chemoattractants (e.g., LCA) and lymphocyte chemotaxis inhibitors provided by the invention, and analogs and derivatives (including fragments) thereof, and neutralizing antibodies thereto and antibody derivatives, (collectively termed herein "Therapeutics") have use prophylactically and therapeutically in diseases or disorders involving inflammation, diseases or disorders which involve extravasation of lymphocytes (inflammatory and immune disorders), and in cancer.

Lymphocyte chemoattractants, and inhibitors of lymphocyte chemoattraction are particularly important therapeutically, because lymphocytes initiate autoimmune and alloimmune diseases.

It should be noted that chemoattractants can be used as either inhibitors or promoters of the inflammatory response depending on how they are administered. For example, a chemoattractant gradient directing leukocytes toward a specific tissue is expected to be pro-inflammatory at such tissue, whereas general systemic administration of a chemoattractant is expected to be inhibitory to leukocyte extravasation, since the systemically administered chemoattractant would competitively inhibit leukocyte recognition of chemoattractant gradients directing its migration toward tissues.

As used herein, a "Promoter Therapeutic" shall be construed as a molecule provided by the invention which promotes the inflammatory response, e.g., a chemoattractant (or functional derivative or analog) locally delivered so as to form a gradient directing lymphocytes toward a specific site in vivo. As used herein, an "Inhibitor Therapeutic" shall be construed as a molecule provided by the invention which inhibits the inflammatory response, e.g., a systemically administered chemoattractant or functional derivative or analog, a chemotaxis inhibitor, chemoattractant receptor (which can, e.g., bind to chemoattractants and thus competitively inhibit the interaction of chemoattractants with their lymphocyte cell-surface receptors), antibodies to chemoattractants and binding domains of such antibodies, etc.

The invention provides methods of reducing inflammation, and of treating or preventing disorders associated therewith, by administration to a subject of an effective amount of an Inhibitor Therapeutic of the invention. In an alternative embodiment, the invention provides methods of stimulating the inflammatory response, and treating or preventing disorders associated with a deficit in the desired inflammatory response, by administration to a subject of an effective amount of a Promoter Therapeutic of the invention.

The subject is preferably an animal, including but not limited to animals such as cows, pigs, chickens, etc., and is preferably a mammal, and most preferably human.

Diseases and disorders which can be treated by administration of a therapeutically effective amount of an Inhibitor Therapeutic include but are not limited to the following:

Inflammatory arthritis—e.g., rheumatoid arthritis, seronegative spondyloarthritites (Behcets disease, Reiter's syndrome, etc.), juvenile rheumatoid arthritis, vasculitis, psoriatic arthritis, polydermatomyositis.

Systemic lupus erythematosus (SLE).

Asthma.

Inflammatory dermatoses—e.g., psoriasis, dermatitis herpetiformis, eczema, necrotizing and cutaneous vasculitis, bullous diseases.

Inflammatory bowel disease—Crohn's disease and ulcerative colitis.

Tissue damage relating to tissue transplantation.

Other autoimmune disorders. In addition to the autoimmune disorders SLE and rheumatoid arthritis, disorders such as glomerulonephritis, juvenile onset diabetes, multiple sclerosis, allergic conditions, autoimmune thyroidiris, allograft rejection (e.g., rejection of transplanted kidney, heart, pancreas, bowel or liver), and graft-versus-host disease can be treated.

In addition, other diseases and clinical correlates of undesirable inflammatory responses can be treated with Inhibitor Therapeutics of the invention, including but not limited to those associated with hemolytic anemia, blood transfusion, certain hematologic malignancies, inflammatory bowel disease, scleroderma, atherosclerosis, cytokine-induced toxicity, necrotizing enterocolitis, granulocyte-transfusion-associated syndromes, Reynaud's syndrome, and other central nervous system inflammatory disorders.

Diseases or disorders that can be treated by the Promoter Therapeutics of the invention include but are not limited to immunosuppression (e.g., due to AIDS, cancer chemotherapy, radiation therapy, corticosteroid therapy, or other therapy for autoimmune disease), and congenital immunodeficiencies.

In a specific embodiment, purified chemoattractant is administered into the bloodstream, to inhibit lymphocyte migration into inflammatory sites and thereby inhibit immune diseases associated with lymphocyte and monocyte emigration such as organ transplant rejection, rheumatoid arthritis, inflammatory bowel disease, psoriasis, asthma, vasculitides, scleroderma, diabetes, and atherosclerosis.

In another specific embodiment, a lymphocyte chemoattractant antagonist, identified by the method described in Section 5.3, is administered by injection into the bloodstream, or into tissue, ingested orally, or by suppository, to inhibit immune diseases associated with lymphocyte and monocyte emigration.

In yet another specific embodiment, a lymphocyte chemoattractant is administered orally or by suppository to attract lymphocytes into the intestine, thus removing them from the body and inhibiting lymphocyte-mediated inflammatory disease.

The invention also provides methods of treating tumors, in particular, malignant tumors, by a method comprising administering a lymphocyte chemoattractant of the invention directly to the site of tumor formation; lymphocytes are thus attracted to the tumor, augmenting leukocyte or immune-mediated regression of the tumor. In a preferred embodiment, a composition comprising a lymphocyte chemoattractant is injected directly into a tumor mass. Tumors which can be thus treated include but are not limited to those of the following types:

Solid tumors
  sarcomas and carcinomas
    fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon carcinoma
    pancreatic cancer
    breast cancer
    ovarian cancer
    prostate cancer
    squamous cell carcinoma
    basal cell carcinoma
    adenocarcinoma
    sweat gland carcinoma
    sebaceous gland carcinoma
    papillary carcinoma
    papillary adenocarcinomas
    cystadenocarcinoma
    medullary carcinoma
    bronchogenic carcinoma
    renal cell carcinoma
    hepatoma
    bile duct carcinoma
    choriocarcinoma
    seminoma
    embryonal carcinoma
    Wilms' tumor
    cervical cancer
    testicular tumor
    lung carcinoma
    small cell lung carcinoma
    bladder carcinoma
    epithelial carcinoma
    glioma
    astrocytoma
    medulloblastoma
    craniopharyngioma
    ependymoma
    pinealoma
    hemangioblastoma
    acoustic neuroma
    oligodendroglioma
    menangioma
    melanoma
    neuroblastoma
    retinoblastoma

5.5.1. DEMONSTRATION OF THERAPEUTIC UTILITY

Compounds demonstrated to have the desired activity in the apparatuses of the invention can be tested in vivo for the desired anti- or pro-inflammatory activity, as the case may be. For example, such compounds can be tested in suitable animal model systems prior to testing in humans, including but not limited to rats, mice, chicken, cows, monkeys, rabbits, etc. Suitable model systems are also used to demonstrate therapeutic utility (see infra).

For in vivo testing, prior to administration to humans, any animal model system known in the art may be used. For example, an animal model system for rheumatoid arthritis is that consisting of animals of the autoimmune MRL/1 mouse strain (Murphy, E. D. and Roths, J. B., 1978, in *Genetic Control of Autoimmune Disease*, Rose, N. R., et al., eds., Elsevier/North-Holland, New York, pp. 207–219), that develop a spontaneous rheumatoid arthritis-like disease (Hang et al., 1982, J. Exp. Med. 155:1690–1701).

Other models for various disorders are known in the art and can be employed, such as those described in the following references:

Canella et at., 1990, "Upregulation and coexpression of adhesion molecules correlate with relapsing autoimmune demyelination in the central nervous system," J. Exp. Med. 172:1521–1524.

Cross et al., 1990, "Homing to central nervous system vasculature by antigen-specific lymphocytes. I. Localization/of $^{14}$C-labeled cells during acute, chronic, and relapsing experimental allergic encephalomyelitis," Lab. Invest. 63:162–170.

García-Vicuña et al., 1992, "VLA family in rheumatoid arthritis: evidence for in vivo regulated adhesion of synovial fluid T cells to fibronectin through VLA-5 integrin," Clin. Exp. Immunol. 88:435–441.

Jiang et al., 1992, "Role of CD8$^+$ T cells in murine experimental allergic encephalomyelitis," Science 256:1213–1215.

Kakimoto et al., 1992, "The effect of anti-adhesion molecule antibody on the development of collagen-induced arthritis," Cell. Immunol. 142:326–337.

Keffer et al., 1991, "Transgenic mice expressing human tumour necrosis factor: a predictive genetic model of arthritis," EMBO J. 10:4025–4031.

Koh et al., 1992, "Less mortality but more relapses in experimental allergic encephalomyelitis in CD8$^{-/-}$ mice," Science 256:1210–1213.

Mori et al., 1992, "Expression of a transgenic T cell receptor β chain enhances collagen-induced arthritis," J. Exp. Med. 176:381–388.

Printseva et al., 1992, "Various cell types in human atherosclerotic lesions express ICAM-1: further immunocytochemical and immunochemical studies employing monoclonal antibody 10F3," Am. J. Pathol. 140:889–896.

Raine, 1991, "Multiple sclerosis: a pivotal role for the T cell in lesion development," Neuropathol. Appl. Neurobiol. 17:265–274.

Shiozawa et al., 1992, "Destructive arthritis without lymphocyte infiltration in H2-c-fos transgenic mice," J. Immunol. 148:3100–3104.

Sollberg et al., 1992, "Elevated expression of β1 and β2 integrins, intercellular adhesion molecule 1, and endothelial leukocyte adhesion molecule 1 in the skin of patients with systemic sclerosis of recent onset," Arthritis Rheum. 35:290–298.

Thorbecke et al., 1992, "Involvement of endogenous tumor necrosis factor α and transforming growth factor β during induction of collagen type II arthritis in mice," Proc. Natl. Acad. Sci. USA 89:7375–7379.

5.5.2. THERAPEUTIC ADMINISTRATION AND COMPOSITIONS

Various delivery systems are known and can be used to administer a Therapeutic of the invention, e.g., encapsulation in liposomes, microparticles, microcapsules, expression by recombinant cells, etc. Other methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local, e.g., direct injection at the inflamed joint of someone suffering from rheumatoid arthritis.

The present invention also provides pharmaceutical compositions. Such compositions comprise a therapeutically effective amount of a Therapeutic, and a pharmaceutically acceptable carrier or excipient. Such a carrier includes but is not limited to saline, buffered saline, dextrose, water, glycerol, ethanol, and combinations thereof. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers or vials filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

5.6. DIAGNOSTIC UTILITIES

The assay of lymphocyte chemotaxis provided by the present invention has diagnostic utility. Such an assay can be used in the diagnosis of a disease or disorder involving a defect in lymphocyte extravasation, by detecting a deficiency in lymphocyte chemotaxis. Thus, a decrease in lymphocyte chemotaxis observed in the assay of the invention in lymphocytes from a patient relative to the chemotaxis observed with lymphocytes of a normal or healthy patient or relative to a standard level known to be exhibited by normal or healthy lymphocytes, indicates the presence of a disease or disorder, particularly one involving a deficiency in lymphocyte chemotaxis, e.g., in lymphocyte extravasation. For example, leukocyte adhesion deficiency (Anderson and Springer, 1987, Ann. Rev. Med. 38:175–194) involves an inherited deficiency in the integrins LFA-1, Mac-1, and p150,95, resulting in deficient adherence of granulocytes, monocytes, and lymphoid cells, which should be detectable in a lymphocyte chemotaxis assay of the invention. In addition, diabetes mellitus, granulocytasthenia, and recurrent pyogenic infections have been reported to involve cell adherence defects (see Gallin et al., 1980, Ann. Int. Med. 92:520–538). Genetic defects in chemoattractant receptors, and/or integrins that interfere with extravasation should be capable of detection by the methods of the invention.

The chemoattractants, and antibodies thereto, also have uses in immunoassays, for measuring the amount of chemoattractant or chemoattractant receptors.

6. A TRANSENDOTHELIAL LYMPHOCYTE CHEMOTAXIS ASSAY

As detailed herein, we have developed a novel transendothelial assay for lymphocyte chemotaxis, with high sensitivity and reliability. The conventional chemotaxis assay (FIG. 1A), and its modification for the transendothelial chemotaxis assay (FIG. 1B) were as follows. Leukocytes were prepared by dextran sedimentation and centrifugation on a Ficoll Hypaque cushion (1.077; Sigma) at 1200 xg for 25 min (Dustin and Springer, 1988, J. Cell Biol. 107:321–31). Peripheral blood mononuclear cells (PBMC) were obtained from the Ficoll Hypaque cushion. Granulocytes were collected from the cell pellet and contaminating erythrocytes were removed by hypotonic lysis. Lymphocytes were enriched and monocytes depleted by incubating the PBMC in RPMI-1640 (Gibco Laboratories, Grand Island, N.Y.) with 5% low-endotoxin fetal calf serum (HyClone Laboratories, Logan, Utah) on tissue culture-treated plastic dishes for two 30 min serial incubations at 37° C., 5% $CO_2$ and collecting the non-adherent cells. During the second enrichment step, leukocytes were fluorescently labeled with 2', 7'-bis-(2-carboxyethyl)-5 (and-6) -carboxyfluorescein (BCECF; Molecular Probes, Inc., Eugene, Oreg.) at 2 µg/ml for 30 min (de Fougerolles et al., 1991, J. Exp. Med. 174:253–267). After incubation., non-adherent cells were collected, washed and resuspended at $5 \times 10^6$ ml in assay medium, a 1:1 mixture of RPMI-1640/M199 (Gibco) plus 1% human serum albumin (HSA). For monocyte chemotaxis experiments, monocytes were recovered from the dishes by treatment with ethylene diamine tetracetic acid (EDTA) and resuspended as described for lymphocytes. Neutrophils were labeled in suspension with BCECF for 30 min at 37° C. and resuspended in assay media at $1.5 \times 10^6$ cells/ml.

Conventional chemotaxis assays utilized Transwell® culture inserts (Transwell® 3422, Costar, Cambridge, Mass.) with 6.5 mm diameter tissue culture-treated, polycarbonate membranes (Capsoni et al., 1989, J. Immunol. Methods 120:125–31; Casale and Abbas, 1990, Am. J. Physiol. 258:C639–47; Partsch et al., 1989, Z. Rheumatol. 48:123–28). Filters with varying pore sizes were used, depending on the cell type being assayed; 3 µm pores were used to measure neutrophil chemotaxis, 5 µm for monocyte chemotaxis and 5 and 8 µm for lymphocyte chemotaxis. In some experiments, Transwells® were pretreated with ICAM-1 (1:20 dilution of purified transmembrane form), collagen (40 µg/ml, Organogenesis, Inc.), or fibronectin (10 µg/ml, Telios, Inc.); this had no significant effect on conventional chemotaxis assays. Chemotactic factors or control media were added, in duplicate or triplicate, to 24-well tissue culture plate(s) in 600 µl final volume. Fluorescently labeled cells were added to the top chamber of each Transwell® in a final volume of 100 µl assay medium. In some experiments, a 1:20 dilution of cells was added to a well containing only a bottom chamber with media. This allowed measurement of the input number of cells. The assay plate(s) was incubated for 4 hr at 37° C., 5% $CO_2$. Following incubation, the Transwells® were removed and the cells in each bottom well were counted by fluorescent microscopy. Cells in the bottom chamber were resuspended by vigorous pipetting and then let settle for about 45–60 minutes until all cells had settled. Five fields of cells were counted per well, using an ocular grid at 100X magnification including the input well, and the number of cells per grid was averaged and presented as percent of input cells migrating to the bottom chamber of the Transwell®. In some experiments, data were presented as "number of cells per grid" and no attempt was made to calculate percent of migrating cells. All samples were run in duplicate or triplicate.

Transendothelial chemotaxis assays utilized human umbilical vein endothelial cells (HUVECs) in passage one to four, cultured on 6.5 mm diameter transwell culture filters in which the tissue culture-treated, polycarbonate membrane (8 µm pore size) had first been treated for at least 0.5 hr at 37° C. with type I collagen (40 µg/ml, Organogenesis, Inc., Canton, Mass.). HUVECs were added to the insert's collagen-coated membrane surface at a concentration of 50,000–100,000 cells/well and were cultured for 5–8 days in M199 medium (Gibco) supplemented with 10–20% low endotoxin fetal calf serum (HyClone), 2 mM L-glutamine, 5 µg/ml gentamicin, 25 mM HEPES, 100 µg/ml porcine intestinal heparin (Sigma), and 100 µg/ml endothelial cell growth factor (Biomedical Technologies, Stoneham, Mass.) at 37° C., 5% $CO_2$. Media was changed every 2 days and confluence was judged by microscopic examination after staining one or more of the monolayers with Wright/Giemsa or the fluorescent label BCECF. Transwells® with unstained confluent endothelial monolayers were then used for assay in the same way as for the conventional chemotaxis assay as described above. A control was usually done to monitor diffusion from the bottom chamber into the top chamber, in order to ensure that components in the bottom chamber did not diffuse too quickly into the top chamber over the course of incubation. This was done by adding fluorescently labeled dextran to the bottom chamber of a Transwell® apparatus, and conducting the assay in the same way as described above. Usually a four- to nine-fold greater level of dextran was present in the bottom chamber relative to the top chamber at the end of the 4 hr incubation time.

Figure 3B:
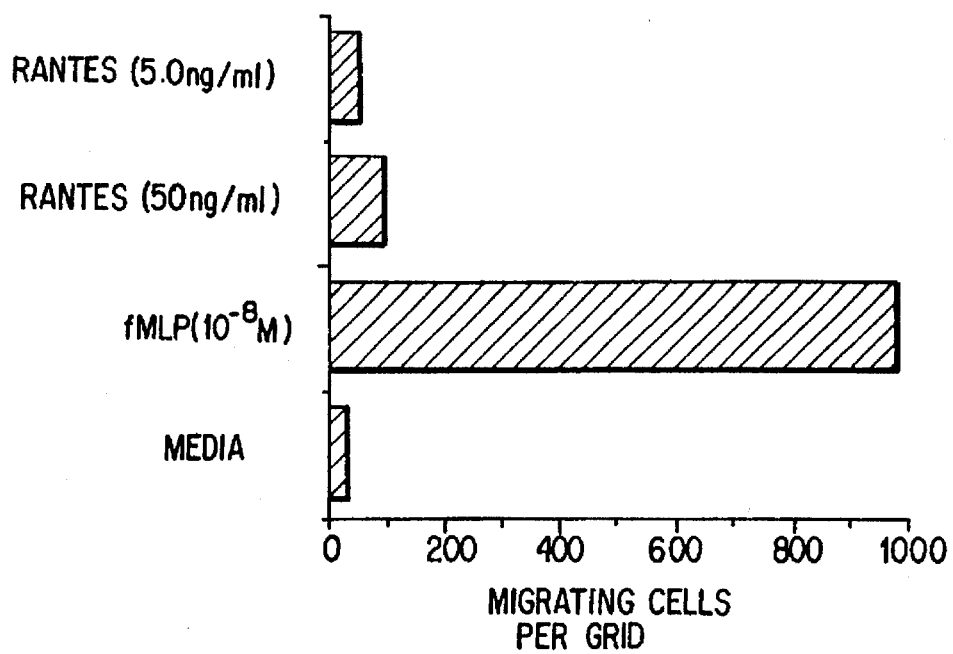
Figure 4A:
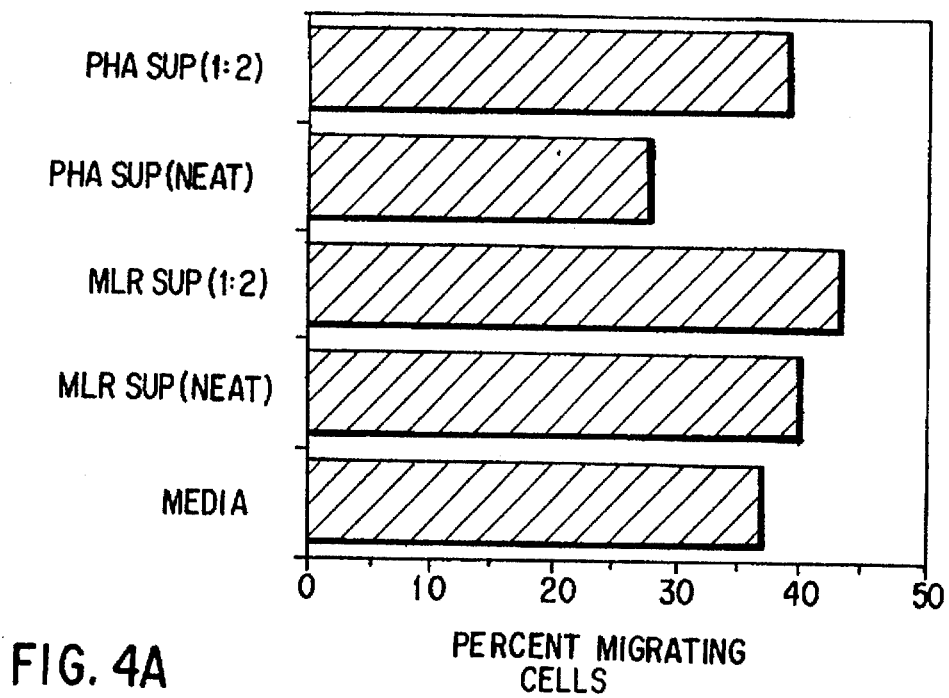

We discovered that lymphocytes behave differently than monocytes and neutrophils in chemotaxis chambers. Neutrophils migrated vigorously to the formylpeptide f-Met-Leu-Phe and IL-8 (FIG. 3A), and monocytes responded well to f-Met-Leu-Phe and much less so to RANTES (FIG. 3B). The response is readily measurable by counting the number of cells that appear in the bottom chamber. Lymphocytes migrated through polycarbonate filters with 5 µm pores but with a very low signal to noise ratio relative to that obtained in the transendothelial assay of the invention (not shown). A high percentage of lymphocytes (30–40%) migrated or fell through polycarbonate filters with 8 µm pores, whether or not chemoattractant was added (FIG. 4A). The same 8 µm filters in the same geometry are used by other investigators to assay for chemotaxis by counting the number of cells that migrate through the filter and stick to the underside (Schall et al., 1990, Nature 347:669–71). However, our results show that these must be numerically a very small percentage of the cells that fall or migrate through the filter. Therefore, these may be assays of sticking rather than chemotaxis.

Figure 4B:
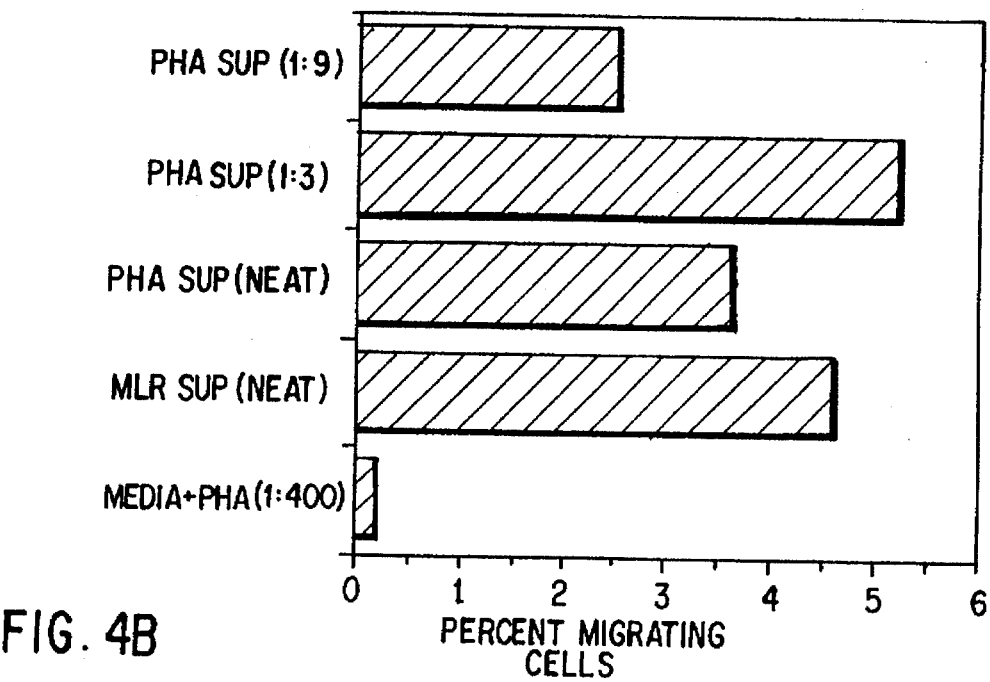

We have thus developed an excellent lymphocyte chemotaxis assay by culturing endothelium on microporous filters coated with collagen or fibronectin and assaying lymphocyte transmigration toward chemoattractants (FIG. 1B, FIG. 4B). A signal to noise ratio of greater than 10 was common, and a response was elicited to supernatants from the mixed lymphocyte reaction (MLR) or phytohemagglutinin (PHA)-stimulated lymphocytes (FIG. 4B). Mixed lymphocyte reaction (MLR) supernatant was generated as described by Bach and Voynow (Bach and Voynow, 1966, Science 153:545–47). Briefly, peripheral blood was drawn from two individuals and prepared as described above. PBMC from one donor were resuspended at $1 \times 10^7$ cells/ml and treated with 50 µg/ml mitomycin C (Sigma) for 20 min at 37° C. (stimulator cells). Following mitomycin C treatment, stimulator cells were washed 3X and resuspended at $2 \times 10^6$ cells/ml. Meanwhile cells from the second donor (responder cells) were enriched for lymphocytes as described above but without the BCECF labeling. Non-adherent cells were collected and resuspended at $2 \times 10^6$ cells/ml. Responder and stimulator cells were combined at a 1:1 ratio in RPMI-1640 supplemented with 5% FCS, 2 mM L-glutamine, and 50 µg/ml gentamicin such that the final concentration of the cells was $4 \times 10^6$ cells/ml. Cultures were incubated at 37° C., 5 % $CO_2$ for 6 days after which supernatant was collected, filtered, and stored at 4° C. For supernatant from PHA-stimulated PBMC, PBMC were obtained from a leukopak (Children's Hospital, Boston, Mass.) by the same methods. PBMC were resuspended at $2-4 \times 10^6$ cells/ml in serum-free media supplemented with 2 mM L-glutamine, 10 mM HEPES, 50 µg/ml gentamicin, 1 µg/ml indomethacin, 3 mM lithium chloride, 50 µM hydroxyurea, and 2.5 µg/ml PHA-P. Cultures were incubated at 37° C., 5% $CO_2$ for 3 days after which supernatant was collected, filtered, and stored at –70° C.

The results with the transendothelial chemotaxis assays (FIG. 4B) were in sharp contrast to assays with microporous membranes alone (FIG. 4A). The transendothelial chemotaxis assay system accurately recapitulates lymphocyte emigration from blood vessels toward chemoattractants in vivo, in which cells migrate through endothelium and basement membrane into tissues. These assay chambers may thus be called a type of "artificial vessel construct."

Other artificial vessel constructs, composed of endothelial cells cultured on matrices of type I collagen, had previously been used to study neutrophil migration toward the chemoattractant IL-8 (Huber et al., 1991, Science 254:99–102). When tested with IL-8 contained in conditioned media from stimulated ECs, neutrophils migrated similarly, and there was a similar signal-to-noise ratio, on collagen matrix plus endothelium and on matrix alone. There was no indication that the assay would be improved for other cell types by adding endothelium, as we have surprisingly shown to be the case for lymphocytes. Indeed, the expectation would have been that neutrophils and lymphocytes would behave similarly.

Lymphocyte migration across endothelium into collagen gels has previously been reported (Kavanaugh et al., 1991, J. Immunol. 146:4149–56; Masuyama et al., 1992, J. Immunol. 148:1367–74). In this system, the endothelium is cultured on a collagen gel formed on a culture dish or well for several days, then lymphocytes are added. However, this is an assay of migration and there is no evidence that chemotaxis is involved; rather, it appears to assay for a migratory subset of lymphocytes. There is no provision for addition of a chemoattractant, and note that, as described below, we find no evidence that endothelium releases a chemoattractant for lymphocytes. Furthermore, lymphocytes migrate into collagen gels even in the absence of an endothelial cell monolayer.

Endothelium may have several properties that enable lymphocyte chemotaxis to be successfully measured. There may be specialized molecules on endothelium such as proteoglycans that retain chemoattractants for presentation to lymphocyte chemoattractant receptors; chemoattractive cytokines such as IL-8 and MCP-1 have heparin binding sites that would enable binding to proteoglycans (Oppenheim et al., 1991, Ann. Rev. Immunol. 9:617–48). LCA also seems to have heparin binding sites as demonstrated by its binding to Heparin-Sepharose during purification (FIG. 10). There could also be specialized endothelial cell surface projections such as microfimbrae that bind to lymphocytes and somehow aid chemotaxis. Finally, endothelial cells form intercellular junctions that impede diffusion of solutes.

We have found that the endothelial cell monolayer significantly retards the diffusion of macromolecules such as fluorescein isothiocyanate (FITC)immunoglobulin and FITC-Dextran (molecular weight 4.4 kD) (FIG. 5). In the absence of endothelium, FITC-Dextran diffuses across filters with 8 µm pores almost to equilibrium in 4 hours. Thus, the gradient at the filter is almost completely dissipated. By contrast, the retardation of diffusion by endothelium results in a sharp gradient, indeed a large step in concentration, immediately at the endothelium. One possible reason for the effectiveness of our assay is that lymphocytes may require steeper chemoattractant gradients that monocytes or neutrophils.

The chemotaxis assay shows excellent dose-response characteristics (FIG. 6). The response was maximal to MLR supernatant that was undiluted (neat) or diluted 1:2, and fell off at greater dilution. This concentration-dependence demonstrates the utility of the assay for measuring chemoattractant in different separations or chromographic fractions during purification and thus in obtaining highly purified material.

We examined several potential chemoattractant sources and lymphokines that have been reported using other assays to have lymphocyte chemoattractant activity, in the transendothelial chemotaxis assay (FIG. 7). We found that IL-1, IL-2, and IL-4 were without effect, in contrast to results previously reported in the less physiologically relevant naked filter chemotaxis assay (Berman et al., 1988, Immunol. Invest. 17:625–77). Endothelial cells failed to release chemoattractants for lymphocytes after 20 hours stimulation with the cytokines IL-4 or IL-1. By contrast, MLR supernatant was highly active as a positive control. There was a much lower response to f Met-Leu-Phe, due to a small percentage of monocytes in the mononuclear cell preparation, as described below.

We examined the effects of known chemoattractive cytokines, and the phenotype of the migrating cells (FIG. 8). The cell preparation routinely used in our assays is mononuclear cells purified by Ficoll-Hypaque gradients. These cells are depleted of monocytes by two cycles of adherence to tissue-culture treated dishes. The cells are >90% lymphocytes, and contain a small percentage (<10%) of monocytes. Transendothelial chemotaxis was carried out in large (24.5 mm) Transwells®. Migrating Cells were stained with mAb to CD3 for T lymphocytes and CD14 for monocytes and the number of cells in each population was quantitated. The MLR supernatant attracted $CD3^+$ T lymphocytes and almost no $CD14^+$ monocytes. By contrast, fMLP was selective for monocytes. MCP-1, MIP-1α, and RANTES, which all belong to the chemokine protein family (Oppenheim et al., 1991, Annu. Rev. Immunol. 9:617–48), showed little if any effect on T lymphocytes. The chemokine IL-8 was also without effect on T lymphocytes (not shown). MCP-lot and RANTES had significant monocyte chemoattractive activity. In conclusion, previously known cytokines or lymphokines cannot account for the lymphocyte chemoattractive activity found in MLR supernatants, and this activity is highly specific for lymphocytes.

We also undertook an analysis of chemotactic versus chemokinetic activity in MLR supernatant. Chemokinesis is defined as stimulated motility that is random in direction, whereas chemotaxis is directional towards the stimulus. A checkerboard analysis, applying the method described by Zigmond and Hirsch (Zigmond and Hirsch, 1973, J. Exp. Med. 137:387–410) to our transendothelial chemotaxis assay, was used to differentiate the specific versus random migration of lymphocytes responding to MLR supernatant. The activity we have defined is directional, because "checkerboard assays" show that lymphocytes migrate when chemoattractant is present in the bottom chamber and not in the top, but that migration falls off as chemoattractant is added to the top chamber (Table I).

TABLE I

CHEMOTACTIC vs. CHEMOKINETIC
ACTIVITY OF MLR SUPERNATANT***

| | TOP | | |
|---|---|---|---|
| BOTTOM | MEDIA | 1:4* | NEAT** |
| MEDIA | 0.10% | 0.13% | 0.78% |
| 1:4* | 3.10% | 1.22% | 0.32% |
| NEAT** | 7.12% | 3.14% | 1.15% |

*MLR supernatant diluted 1:4 with media was used.
**NEAT = undiluted MLR supernatant
***Data is presented as percentage of input lymphocytes which migrate into the bottom chamber.

This finding in our artificial vessel construct demonstrates that adding chemoattractant to the vessel side inhibits chemotaxis. Thus, administering chemoattractant into the bloodstream of patients should block chemotaxis of lymphocytes into sites of inflammatory disease by inhibiting the response toward chemoattractants present in the diseased tissue.

We have thus far examined responses to supernatants of several types of cultured leukocytes and cell lines. PHA-stimulated lymphocytes consistently release the same or greater activity than MLR cultures in serum-free medium. The migrating cells have the same phenotype of $CD3^+$ lymphocytes as found for MLR supernatant (FIG. 9).

7. CHARACTERIZATION OF A NOVEL LYMPHOCYTE CHEMOATTRACTANT

The lymphocyte chemoattractant (termed "LCA") we identified as present in media conditioned by PHA-activated PBMC was concentrated and then purified and characterized as to size as described below.

A two-step purification protocol was developed. Media conditioned by PHA-activated PBMC was applied to a Heparin-Sepharose column (FIG. 10) using a salt gradient for elution. LCA was eluted at a salt concentration of approximately 0.55M NaCl. Following Heparin-Sepharose chromatography, the active fractions were pooled, concentrated, and LCA further purified by size exclusion chromatography (FIG. 11). The molecular weight of LCA following the sequential use of Heparin-Sepharose affinity chromatography and size exclusion chromatography was 14,500±3,000 daltons. Following size exclusion chromatography, the chemoattractant preparation was subjected to reverse phase high performance liquid chromatography (FIG. 12).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for detecting or measuring lymphocyte chemotaxis comprising detecting or measuring the transmigration of lymphocytes completely through a filter in a direction (a) toward increased levels of a known or suspected lymphocyte chemoattractant, and (b) from a first surface of the filter toward an opposite, second surface of the filter; wherein said filter is a microporous filter having on its first surface an endothelial cell monolayer; and wherein the presence and amount of said transmigration of lymphocytes completely through the filter indicates the presence and amount, respectively, of lymphocyte chemotaxis.

2. A method for identifying a lymphocyte chemoattractant comprising detecting lymphocyte chemotaxis according to the method of claim 1, in which said transmigration is toward increased levels of a suspected chemoattractant, and in which the detection of said transmigration indicates that the suspected chemoattractant is a chemoattractant.

3. The method according to claim 1 in which the microporous filter has a pore size in the range of 3–8 microns.

4. The method according to claim 1 in which the microporous filter has a pore size in the range of 5–8 microns.

5. The method according to claim 4 in which the endothelial cell is an umbilical vein endothelial cell.

6. The method according to claim 1 in which the lymphocytes are labelled.

7. The method according to claim 6 in which the label is fluorescent.

8. A method of diagnosing an inflammatory disorder in a patient comprising measuring lymphocyte chemotaxis according to the method of claim 1, in which said lymphocytes are from the patient; and said transmigration is toward known lymphocyte chemoattractant molecules; in which a decrease in the measured amount of lymphocyte chemotaxis relative to the level observed with lymphocytes from a healthy individual or from the patient prior to disease onset or in remission, indicates the presence of an inflammatory disorder.

9. A method for detecting or measuring lymphocyte chemotaxis comprising:

(a) incubating an apparatus for a time period sufficient to allow any chemotaxis of lymphocytes to occur, in which said apparatus comprises:
  (i) a microporous filter;
  (ii) an endothelial cell monolayer on an upper surface of said filter;
  (iii) a first chamber having an opening communicating with said endothelial cell monolayer, said first chamber containing a first composition, said first composition comprising a first fluid and lymphocytes; in which said first fluid contacts said endothelial cell monolayer; and
  (iv) a second chamber having an opening communicating with a lower surface of said filter; in which said second chamber contains a second composition; said second composition (A) comprising a second fluid contacting the lower surface of said filter, and (B) comprising or suspected of comprising molecules having lymphocyte chemoattractive activity; and (b) measuring the amount of lymphocytes in the second chamber, in which an increased amount of lymphocytes in the second chamber relative to the baseline amount present when said second composition does not comprise a lymphocyte chemoattractant indicates that lymphocyte chemotaxis has occurred, and in which the difference between said increased amount and the baseline amount indicates the amount of lymphocyte chemotaxis.

10. The method according to claim 9 in which the first composition has a cell population that is greater than 85% lymphocytes.

11. A method for identifying a lymphocyte chemoattractant comprising detecting lymphocyte chemotaxis according to the method of claim 10, in which the detection of lymphocyte chemotaxis indicates that said molecules comprised in the second composition are lymphocyte chemoattractants.

12. A method for identifying a lymphocyte chemoattractant comprising detecting lymphocyte chemotaxis according to the method of claim 9, in which the detection of lymphocyte chemotaxis indicates that said molecules comprised in the second composition are lymphocyte chemoattractants.

13. The method according to claim 9 in which the amount of lymphocytes in the second chamber measured in step (d) is calculated as the ratio of the number of lymphocytes present in the second chamber to the number of lymphocytes in said first composition.

14. A method for detecting or measuring lymphocyte chemotaxis comprising detecting or measuring the transmigration of lymphocytes completely through a filter, in a direction (a) toward increased levels of a known or suspected lymphocyte chemoattractant, and (b) from a first surface of the filter toward an opposite, second surface of the filter; wherein said filter has a pore size in the range of 5–8 microns, and said filter has on its first surface a human umbilical vein endothelial cell monolayer; and wherein the presence and amount of said transmigration of lymphocytes completely through the filter indicates the presence and amount, respectively, of lymphocyte chemotaxis.

15. The method according to claim 14 in which the lymphocytes are labeled.

16. The method according to claim 15 in which the lymphocytes are fluorescently labeled.

17. The method according to claim 16 in which the lymphocytes are labeled with fluorescein or a derivative thereof.

18. A method for identifying a lymphocyte chemoattractant comprising detecting lymphocyte chemotaxis according to the method of claim 14, in which said transmigration is toward increased levels of a suspected chemoattractant, and in which the detection of said transmigration indicates that the suspected chemoattractant is a chemoattractant.

19. A method for detecting or measuring lymphocyte chemotaxis comprising:
(a) incubating an apparatus for a time period sufficient to allow any chemotaxis of lymphocytes to occur, in which said apparatus comprises:
  (i) a filter having a pore size in the range of 5–8 microns;
  (ii) a human umbilical vein endothelial cell monolayer on an upper surface of said filter;
  (iii) a first chamber having an opening communicating with said endothelial cell monolayer; said first chamber containing a first composition, said first composition comprising a first fluid and lymphocytes, in which said first fluid contacts said endothelial cell monolayer; and
  (iv) a second chamber having an opening communicating with a lower surface of the filter; in which said second chamber contains a second composition, said second composition comprising (A) a second fluid contacting the lower surface of the filter, and (B) molecules having or suspected of having lymphocyte chemoattractive activity;
(b) measuring the amount of lymphocytes in the second chamber, in which an increased amount of lymphocytes in the second chamber relative to the baseline amount present when said second composition does not comprise a lymphocyte chemoattractant indicates that lymphocyte chemotaxis has occurred, and in which the difference between said increased amount and the baseline amount indicates the amount of lymphocyte chemotaxis.

20. The method according to claim 19 in which the first composition has a cell population that is greater than 85% lymphocytes.

21. A method for identifying one or more lymphocyte chemoattractants comprising detecting lymphocyte chemotaxis according to the method of claim 14, in which the detection of lymphocyte chemotaxis indicates that said molecules comprised in the second composition are lymphocyte chemoattractants.

22. A method for identifying a lymphocyte chemoattractant comprising detecting lymphocyte chemotaxis according to the method of claim 19, in which the detection of lymphocyte chemotaxis indicates that said molecules comprised in the second composition are lymphocyte chemoattractants.

23. A method for detecting a lymphocyte chemoattractant antagonist comprising:
(a) incubating an apparatus for a time period sufficient to allow any chemotaxis of lymphocytes to occur, in which said apparatus comprises:
  (i) a microporous filter;
  (ii) an endothelial cell monolayer on an upper surface of said filter;
  (iii) a first chamber having an opening communicating with said endothelial cell monolayer, said first chamber containing a first composition, said first composition comprising (A) a first fluid contacting said endothelial cell monolayer, (B) test molecules, and (C) lymphocytes; and
  (iv) a second chamber having an opening communicating with a lower surface of said filter, in which said second chamber contains a second composition; said second composition comprising (A) a second fluid contacting the lower surface of said filter, and (B) lymphocyte chemoattractant molecules;
(b) measuring the amount of lymphocytes in the second chamber, in which a decreased amount of lymphocytes in the second chamber relative to the amount of lymphocytes in the second chamber measured when the first composition does not contain the test molecules, indicates that the test molecules are lymphocyte chemoattractant antagonists.

* * * * *